(12) United States Patent
Boder et al.

(10) Patent No.: US 12,128,273 B2
(45) Date of Patent: Oct. 29, 2024

(54) VOCAL TRAINING DEVICE

(71) Applicant: Rayvox Ltd., London (GB)

(72) Inventors: Oren Boder, London (GB); Edward Handford, London (GB)

(73) Assignee: Rayvox Ltd., London (GB)

( * ) Notice: Subject to any disclaimer, the term of this patent is extended or adjusted under 35 U.S.C. 154(b) by 153 days.

(21) Appl. No.: 18/000,379

(22) PCT Filed: Jun. 1, 2021

(86) PCT No.: PCT/GB2021/051346
§ 371 (c)(1),
(2) Date: Nov. 30, 2022

(87) PCT Pub. No.: WO2021/245402
PCT Pub. Date: Dec. 9, 2021

(65) Prior Publication Data
US 2023/0218945 A1 Jul. 13, 2023

(30) Foreign Application Priority Data

Jun. 1, 2020 (GB) ..................................... 2008209

(51) Int. Cl.
*A63B 23/025* (2006.01)
*A63B 23/18* (2006.01)
*G09B 15/00* (2006.01)

(52) U.S. Cl.
CPC ............ *A63B 23/025* (2013.01); *A63B 23/18* (2013.01); *G09B 15/00* (2013.01)

(58) Field of Classification Search
CPC ....... A61B 5/097; A63B 23/025; A63B 23/18; A63B 23/03; A63B 23/032; G09B 15/00
See application file for complete search history.

(56) References Cited

U.S. PATENT DOCUMENTS 10,335,635 B2 * 7/2019 Kezirian ............ A63B 21/0085
11,794,072 B2 * 10/2023 Lundquist .............. G09B 19/00
(Continued)

FOREIGN PATENT DOCUMENTS

CN 204483739 U 7/2015
CN 207833725 U 9/2018
(Continued)

OTHER PUBLICATIONS

International Search Report and Written Opinion of International Application No. PCT/GB2021/051346, dated Nov. 3, 2021, 13 pp.
(Continued)

*Primary Examiner* — Megan Anderson
(74) *Attorney, Agent, or Firm* — Shumaker & Sieffert, P.A.

(57) ABSTRACT

A vocal training device comprises a generally cylindrical hollow body. The generally cylindrical hollow body has a first open end, a second open end, a first tube member and a second tube member. The second tube member is configured to be telescopically inserted into the first tube member, such that the length of the generally cylindrical hollow body of the vocal training device is adjustable. The vocal training device also has a connector having a portion that is configured for removable connection to the second open end of the generally cylindrical hollow body of the vocal training device and a portion configured for removable connection to a vocal training attachment member. The vocal training attachment member can be an aperture reducing attachment, a variable aperture reducing attachment, a breath visualisation attachment, a water resistance voice therapy training attachment or an oscillating resistance generator.

19 Claims, 19 Drawing Sheets

(56) References Cited

U.S. PATENT DOCUMENTS

| | | | |
|---|---|---|---|
| 2009/0159062 A1* | 6/2009 | Bohman | A63B 21/0085 |
| | | | 128/202.13 |
| 2017/0348504 A1 | 12/2017 | Denizoglu | |
| 2018/0050169 A1 | 2/2018 | Denizoglu | |
| 2019/0105534 A1 | 4/2019 | Lundquist | |
| 2022/0175272 A1* | 6/2022 | Darlington | A61B 5/082 |

FOREIGN PATENT DOCUMENTS

| CN | 108682224 A | 10/2018 |
|---|---|---|
| CN | 208405942 U | 1/2019 |
| CN | 110384380 A | 10/2019 |

OTHER PUBLICATIONS

Search Report from counterpart GB Application No. 2008209.5, dated Oct. 20, 2020, 3 pp.

\* cited by examiner

VOCAL TRAINING DEVICE

This application is a national stage application under 35 U.S.C. § 371 of PCT Application No. PCT/GB2021/051346, filed 1 Jun. 2021, which claims the benefit of Great Britain Application No. 2008209.5, filed 1 Jun. 2020. The entire contents of each of PCT/GB2021/051346 and Great Britain Application No. 2008209.5 are incorporated herein by reference in their respective entireties.

The present invention is concerned with a vocal training device. The present invention is particularly concerned with an improved vocal training device for semi-occluded vocal tract (SOVT) exercises.

The vocal folds (vocal cords) are two bands of smooth muscle tissue found in the larynx (voice box) in a person's neck at the top of the trachea (windpipe). As air passes through the vocal folds from a person's lungs, the vocal folds vibrate or oscillate. The vibration of the vocal folds produces the sound of the person's voice. In order for the vocal folds to vibrate, the pressure of air passing through the vocal folds must exceed a 'phonation threshold pressure' (PTP). Once the PTP is reached, the bottom of the vocal folds open. As air passes through the vocal folds, the bottom part of the vocal folds begins to close, which allows the sub-glottal pressure (the pressure below the vocal folds) to build up until the PTP is, once again, reached. The vocal folds oscillate in this way hundreds of times per second in order to produce sound.

The vocal folds will only vibrate if they have sufficient elastic potential to come back together again. If the vocal folds are stiffened, or otherwise fatigued, the vocal folds will be unable to properly comply with the pressure systems imparted on them.

Phonation (the production of sound) takes significant effort for an individual, especially singers, speakers or professional voice users, as the vocal folds are continually having to resist the increasing pressure of the lungs, as well as deal with the collision forces experienced each time the vocal folds close and the cyclical stretching and compressing of the vocal folds.

SOVT exercises have been proven to help people sing with ease, alleviate vocal tension, achieve good vocal fold (or vocal cord) closure, strengthen the muscles of a person's voice, recover fatigued vocal folds, help gain vocal power without straining, and provide a protective 'air cushion' buffer at a person's vocal folds.

In SOVT exercises, there is a partial closure or narrowing at some point of a person's vocal tract above the vocal folds. In active SOVT exercises, a person's lips or tongue is manipulated in order to create the occlusion. The person manually controls, shapes and positioned their lips and/or tongue in order to vary the outflow of air. In passive SOVT exercises, a device such as a straw, tube or specialised SOVT device is used to create the occlusion. This is advantageous as it means the user is able to relax and avoid secondary issues that are associated with holding the jaw or tongue in tension.

SOVT exercises are beneficial as the narrowing of the vocal tract restricts the amount of air that can escape the system which introduces a back pressure of reflected air and acoustic energy which is inversely proportional to the aperture of the system. Generally, the narrower the aperture, the greater the back pressure. The reflected air and acoustic energy provide a number of advantageous mechanical functions.

Firstly, the reflections reduce the PTP. The reflected back pressure helps the bottom of the vocal folds to open more easily, and also helps to optimally position and shape the top of the vocal folds, thereby bringing them back into alignment.

Secondly, new pressure systems within the vocal folds (intra-glottal pressure) provide 'air cushions' in the spaces between the vocal folds. These air cushions help to reduce the collision forces between the vocal folds with each oscillation.

Thirdly, the build-up of pressure above the vocal folds helps the vocal folds to resist the intensity of the increasing sub-glottic pressure by the lungs, which is particularly important in individuals who overcompensate and build up too much lung pressure.

The reflected acoustic energy also helps to maintain the vocal fold vibrations, which means that the voice user needs to do less work to keep the vocal folds moving.

Known SOVT exercise devices range from simple straws which, in effect, extend the length of the vocal tract, to more complex apparatus with water chambers and tubes.

Straws are advantageous as they are simple and easy for a person to transport, which is particularly beneficial for people who travel between venues to sing or speak and use the SOVT straw for warming up and cooling down their voice prior to or following a performance or speech. The use of plastic straws, however, contributes to plastic pollution which is detrimental to the environment. This disadvantage has been addressed by the production of SOVT straws which are manufactured from metals, for example as described in US patent application published as US 2019/0105534. A further disadvantage, common to both plastic and metal straws, is that it is not possible to vary the resistance offered by the straw since the length and the diameter of the opening of the straws is fixed.

Apparatus including water chambers and tubes, for example as described in US patent application published as US 2017/0348504, allow the resistance to be changed by changing the amount of water within the chamber. These devices are, however, less convenient for a user to take to performances or speeches as they are bulky, include breakable components and require water. These devices are also more complex, and costly, to manufacture.

While SOVT straws are simple and portable, their aperture is fixed which limits the resistances which can be obtained. Furthermore, such straws do not provide a user with any feedback.

It is an aim of the present invention to overcome one or more of the aforementioned disadvantages which are associated with known SOVT devices.

According to a first aspect of the invention, there is provided a vocal training device comprising:
  a generally cylindrical hollow body having:
    a first open end;
    a second open end;
    a first tube member; and,
    a second tube member;
  wherein the second tube member is configured to be telescopically inserted into the first tube member, such that the length of the generally cylindrical hollow body of the vocal training device is adjustable; and,
  wherein the vocal training device further comprises:
    a connector having a portion that is configured for removable connection to the second open end of the generally cylindrical hollow body of the vocal training device, and a vocal training attachment member that is configured for removable connection to the connector.

The provision of a connector advantageously allows vocal training attachment members to be connected to the telescopic vocal training device.

The vocal training device may also include a third tube member. The third tube member may be configured to be telescopically inserted into the second tube member, such that the length of the generally cylindrical hollow body of the vocal training device is adjustable.

The addition of a third tube member further increases the resistances that can be offered by the vocal training device.

The telescopic arrangement of the first, second and third tube members allows the resistance of the vocal training device to be easily adjusted according to a user's requirements. The longer the length of the device, the greater the resistance it will have. In contrast, the shorter the length of the device, the less resistance it will have.

The length of a user's vocal tract is extended by the length of the device which extends outside of the user's body. The vocal benefits to this include lowering and stabilising the passagio (voice break), as well as to allow for more resonance. A further advantage of the telescopic device is, therefore, to give the user the ability to lengthen their vocal tract as required for their unique voice, such that they can manipulate where their break might fall in order to smooth over/"work-out" the notes affected.

The adjustable length of the vocal training device also allows for variability in smoothing out the airflow—i.e., the airflow becomes less turbulent. This is advantageous as when the airflow becomes too turbulent, more pressure is required to maintain the sound, which is not ideal for singers. Essentially, the pressure difference between the systems would be increased, so the muscles would need to work even harder to do their jobs. Having the ability to make the airflow more linear also allows a user to better manage their air pressure according to their unique physiology.

The portion of the connector that is configured for removable connection to the second open end of the generally cylindrical hollow body may be a first portion. The connector may also have a second portion that is flared such that an outer diameter of the flared second portion is greater than an outer diameter of the first portion.

The flared end acts as a smooth transition to atmosphere, which offers a reduction in the resistance provided by the vocal training device.

The generally cylindrical hollow body may have a first internal diameter at the first open end and a second internal diameter at the second open end. The second internal diameter may be less than the first internal diameter.

As the diameter of the body decreases along its length, the pressure increases. This means that there will be more resistance within the device. So, if a user blows through the device from the first open end (the widest end) to the second open end (the narrowest end), there will be a greater resistance. This will give a "harder" vocal workout. In contrast, if the user reverses the device (and thus the flow direction through it), i.e., blowing from the second open end to the first open end, then the resistance will decrease thereby giving an "easier" vocal workout. In this way, the range of resistances that can be offered by the vocal training device is further increased. A user will, advantageously, be able to adjust the resistance on another axis, so not just with the length adjustments, but also by taking advantage of the differences between the diameters of the first and second open ends.

The connector may have a third internal diameter. The third diameter may be greater than the second diameter.

The tube members that form the telescopic cylindrical hollow body may be assembled by any convenient method. In one arrangement, adjacent tube members may be retained together by means of a telescopic connector and an O-ring. For example, and with reference to FIG. 4 of the accompanying drawings, a first telescopic connector may be crimped onto the second tube (diameter B) to create a secure coupling. This crimping process also creates a slight radial notch on the outer surface of the tube body. Then an O-ring is fitted onto the left-most un-crimped and exposed side of the first telescopic connector.

The largest tube (diameter A) is provided with a slight lip at one of its ends. The assembly is then fed through the largest tube via the end with no lip. The O-ring creates an interference fit and seal when inserted, and provides a smooth surface to accommodate the telescoping action.

As the first telescopic connector and second tube assembly is pulled through the largest tube, the notch of the second tube interferes with the lip of the largest tube, preventing removal.

Once all pieces have been suitably inserted following this procedure, the first end of the largest tube may also be rounded to create a lip. This now prevents any of the pieces from escaping the assembly, and the tubes are free to move between a compact and extended positioning without decoupling or falling apart.

The telescopic connector and crimp further provide the system with strength and rigidity so as to prevent flexing/bending at the joining areas, and also stops the user from being able to pull the tubes apart accidently or on purpose.

The vocal training attachment members offers the advantage of allowing the resistance provided by the device to be optimised according to a user's need and/or for feedback on the exercise to be provided to a user.

The vocal training attachment member may be an aperture reducing attachment.

The inclusion of an aperture reducing attachment further increases the resistances that can be offered by the vocal training device.

The aperture reducing attachment may have a fourth internal diameter. The fourth internal diameter may be less than the second internal diameter.

The vocal training attachment member may be a variable aperture reducing attachment.

The variable aperture reducing attachment allows the resistance provided by the device to be optimised according to a user's needs.

The variable aperture reducing attachment may comprise an inner tubular body having an opening in the body wall and an outer tubular body or sleeve which is also provided with an opening in its sleeve wall. An aperture is created in the attachment when there is overlap between the respective openings of the inner and outer bodies, and the size of the aperture may be varied by rotating the outer body relative to the inner body to increase or decrease the degree of overlap.

The sleeve and inner body may be retained together by an interference fit, such as by means of an O-ring, to permit rotation of the sleeve around the inner body only when a torque is applied.

In one embodiment, the variable aperture reducing attachment may include a slot. The slot may be generally triangular. The variable aperture reducing attachment may also include an outer sleeve having an opening. The opening may be generally rectangular. The outer sleeve may be configured to be rotatable relative to the variable aperture reducing attachment member such that the position of the generally rectangular opening relative to the slot can be varied. For example, the outer sleeve may be configured to be rotatable relative to the variable aperture reducing attachment member such that there is no overlap between the opening and the slot and hence the aperture is closed. As the outer sleeve is further rotated, the opening and the slot come into alignment and the degree of overlap between the opening and the slot gradually increases, providing an aperture of increasing size, until it reaches maximum overlap and hence a maximum aperture size; with yet further rotation the degree of overlap diminishes and ultimately returns to a closed aperture. In such an embodiment a user is free to continually vary the size of the aperture from minimum (closed) to maximum (fully open) positions.

In an alternative embodiment, the variable aperture reducing attachment may include a variable aperture reducing attachment member provided with a plurality of openings having a range of different diameters. The variable aperture reducing attachment may also include an outer sleeve provided with a slot. The outer sleeve may be configured to be rotatable relative to the attachment member such that as the sleeve is rotated the slot comes into alignment with different openings. The slot on the outer sleeve and the arrangement of the openings on the attachment member may be configured such that when one opening is fully revealed no other openings are visible.

In this alternative embodiment, a user is able definitively to set a resistance value in a reliable, replicable way. Further, the attachment member may include indicia adjacent the openings and visible through the slot to provide an indication to the user as to the setting selected. Accordingly, it is easy for the user to be able to return to their preferred configuration for vocal training.

In one arrangement, the openings on the inner body are provided radially, in a plurality of rows, and the openings in one row are offset relative to the openings in the other row or rows. For example, the openings may be provided in an upper row and a lower row. The openings may be circular and may range from 1 mm to 4.5 mm in diameter in increments of 0.5 mm, with eight openings in total.

The vocal training attachment member may be a breath visualisation attachment.

The breath visualisation attachment provides a user with feedback on their technique during use of the vocal training device.

The breath visualisation attachment may include a fan. The fan may be provided on an exterior surface of the breath visualisation attachment.

The fan advantageously provides a biofeedback mechanism. With a fan positioned on an exterior surface of the breath visualisation attachment, a user is able to visualise their airflow in real time, which is not generally possible without the need for either specialised scientific equipment, or by placing a device in water and monitoring the bubbles produced during use of the device. This biofeedback is an essential part of understanding and controlling airflow, which is vital for singing correctly. It allows the user to very accurately see and respond to something previously 'invisible'. The breath visualisation attachment provides a very compact, portable solution.

If desired, the fan attachment can also be used with water in order to generate resistance. This is because a user will need to displace the water and rotate the fan whilst breathing out, which is more difficult to do as compared to either displacing the water or rotating the fan.

Conducting vocal training exercises by submersing an end of the training device in water provides additional benefits for the user since the resulting bubbles create an automatic variable resistance which produces a massage effect on the vocal tract, whereas when not submersed there is a continuous back pressure (i.e., the pressure is not oscillating) on the vocal tract and hence a stronger loading of the vocal folds.

The vocal training attachment member may be a water resistance voice therapy (WRVT) training adapter.

The WRVT training adapter may comprise a curved tubular extension member having a distal end configured for removeable connection to the connector and a proximal end angularly offset with respect to the distal end wherein in use the adapter enables the hollow cylindrical body to be aligned in a substantially vertical orientation when a user adopts a normal upright posture.

The WRVT training adapter according to the present invention enables improved head/neck alignment when a user practices WRVT exercises. Without the adapter, a user opting to use the vocal training device for WRVT exercises would undesirably compromise the head/neck by unnaturally adjusting their posture so that the "straw" aligns vertically in the water and thus avoids spillages. Such a head/neck position may prevent free movement of the larynx and cause muscle tension. Accordingly, use of the WRVT training adapter enables the user to adopt a more suitable and natural posture, for example by using the I end of the adapter adjacent the proximal end as a mouth piece so that the hollow cylindrical body may then be substantially vertically aligned when the first end is submersed in water.

The curved tubular extension member may include a first extension portion that extends from the distal end and aligns in use with the longitudinal axis of the generally cylindrical hollow body of the training device and a curved portion interposed between the first extension portion and the proximal end. To allow the user to maintain their natural posture whilst using the device, the bend angle of the curved portion may be in the region of 30 to 60° and preferably about 45°.

A second extension portion may be provided between the curved portion and the proximal end. The second extension portion may be shorter than the first extension portion. The second extension portion may be used as a mouth piece. The first extension portion, curved portion and second extension portion together may form a J-bend tube.

It will be understood that the WRVT training adapter is multi-functional and may be used as an attachment member not only with a vocal training device according to the present invention, but may similarly be used with other SOVT straws, and allows users to more comfortably undertake WRVT exercises with the end of the straw submersed in water. Accordingly, from another aspect, the invention further resides in a WRVT training adapter for an SOVT straw, the adapter comprising a curved tubular extension member having a distal end configured for removeable connection to an end of a SOVT straw and a proximal end angularly offset with respect to the proximal end, wherein the adapter enables the straw to be aligned in a substantially vertical orientation in use when a user adopts a normal upright posture.

The WRVT training adapter may connect to the body of the training device or SOVT straw at its distal end via an interference fit or via complementary screw threads. For example, when used with the training device according to the present invention, the distal end may comprise a male screw threaded portion for connection to a female screw threaded portion on the connector.

The vocal training attachment member may be an oscillating resistance generator.

The oscillating resistance generator may comprise a substantially hollow body having a proximal end configured for removeable connection to the connector and a distal end optionally configured for removeable connection to other vocal training attachment members, and an air flow moderator housed within the hollow body for providing air pressure oscillation as air flows from the proximal end towards the distal end.

In one arrangement, the air flow moderator may comprise a fan assembly having a fan element that freely spins under the influence of air flowing through the hollow body for re-directing airflow during a spin cycle, and a plate having a plurality of apertures of different sizes disposed in the hollow body downstream of the fan assembly through which in use air is alternately directed by the fan element to generate an oscillating air flow.

The oscillating resistance generator offers a user a similar experience to WRVT exercises but without the need for water. In particular, it will be understood that as air moves through the fan assembly, the fan element begins to spin and hence air is directed in turn to each of the apertures in the plate thereby creating oscillation in the air pressure. This oscillation mimics the effect of using the vocal training device in water but advantageously removes the need for water in order to practice WRVT exercises.

The aperture plate may be positioned directly adjacent to the fan element for better effect. The aperture sizes in the plate may be selected for producing a required amplitude and oscillation frequency, allowing for a slower, more gentle massage effect or a faster, more intense effect. The plate may have two apertures disposed on opposing halves of the plate, a larger diameter one and a smaller diameter one. For example, a plate having a 4 mm aperture and a 2 mm aperture offers a suitable binary resistance difference, but other aperture sizes may equally be used.

The oscillating resistance generator may be supplied with a plurality of plates having apertures in a range of different sizes allowing a user to select a desired plate according to their individual preference. Further, the hollow body of the oscillating resistance generator may include a closure member, or lid, allowing access to the interior for replacement of the plate.

The fan element may be a spiral element and directs air flow according to the position of the spiral element as it rotates.

It will be understood that the oscillating resistance generator may be used as an attachment member not only with a vocal training device according to the present invention, but may similarly be used with other SOVT straws, and allows users to mimic WRVT exercises without any need for water.

The oscillating resistance generator may connect to the body of the training device or SOVT straw at its proximal end via an interference fit or via complementary screw threads. For example, when used with the training device according to the present invention, the proximal end may comprise a male screw threaded portion for connection to a female screw threaded portion on the connector. Moreover, the oscillating resistance generator may be used with other training attachments, for example by a removeable connection at the distal end.

From another aspect, the vocal training device may include a mouth piece configured for removable connection to an open end of the generally cylindrical hollow body of the vocal training device. The mouth piece may be directly connected to an open end of the hollow body, or indirectly connected for example via the connector.

In one embodiment, the mouth piece comprises a hollow cylindrical attachment having a distal open end for removable connection to an open end of the generally cylindrical body and a proximal open end around which a user seals their lips in use, wherein the internal diameter of the hollow attachment is substantially uniform across its length and corresponds to the internal diameter of the cylindrical hollow body at the end where it is connected, and the external diameter at the proximal end of the attachment is greater than the external diameter of the cylindrical body at the said end thereby to provide an enlarged surface area for interfacing with a user's lips.

Since the internal diameters of the mouth piece and cylindrical body are the same where the mouth piece connects to the body, the mouth piece does not alter the resistance values offered by the cylindrical hollow body of the device. However, the mouth piece provides the device with a region of expanded external diameter as compared with the generally cylindrical hollow body and around which a user's lips can more comfortably form a seal. Thus, when the mouth piece is used, a user does not need to overly tighten their lips to seal around the outside of the main body of the device, but instead creates a seal with the expanded outer diameter portion of the mouth piece.

The mouth piece may be configured for removable connection to the first open end of the generally cylindrical hollow body. In such an arrangement, the mouth piece may be used in conjunction with a vocal training attachment member connected at the second open end via the connector.

The mouth piece may be removably connected to the cylindrical hollow body, for example, by means of an interference fit, or via a screw thread at its distal end for cooperation with a complementary thread on the cylindrical hollow body or on the connector. In one arrangement, the distal end of the mouth piece is provided with an external thread for connecting to an internal thread at the first open end of the hollow body or to an internal thread on the connector.

The proximal end of the mouth piece adapter may have a bevelled, chamfered or rounded edge for the comfort of the user.

From yet another aspect, the invention resides in a mouth piece adapter configured for removable connection to a plurality of vocal training devices of different sizes, the adapter comprising a hollow cylindrical attachment having a proximal open end for providing an interface with a user's lips and a distal open end for connection to an open end of a hollow cylindrical body of a training device, wherein the distal open end of the adapter has an internal diameter configured to receive and retain the open end of a first hollow cylindrical body and has an external diameter configured to be received within and be retained by the open end of a second hollow cylindrical body.

By means of the aforementioned mouth piece adapter, it is possible to fit a mouth piece on vocal training devices with hollow cylindrical bodies of different internal diameters; the distal end of the adapter being fitted either by slotting over a narrower diameter open end or by inserting into a wider diameter open end of the hollow cylindrical body.

The mouth piece adapter may be configured to slot over the open end of the hollow cylindrical body of the vocal training device according to the first aspect of the invention. In this way, the resistance values offered by the body remain substantially unchanged as the internal diameter of the body is not restricted.

The mouth piece adapter may be configured to connect with the hollow cylindrical body of the training device by an interference fit.

In order for a user to know when the mouth piece adapter has been inserted into or slotted over the open end of the hollow cylindrical body to an optimum position, the adapter may be provided with an abutment against which the open end abuts when optimally positioned. For example, the adapter may be provided with a collar between its distal and proximal ends against which the open end of the hollow cylindrical body abuts when the distal end of the adapter is fully inserted into the open end. The adapter may be provided with a protrusion extending into the bore of hollow cylindrical attachment against which the open end of the hollow cylindrical body abuts when the open end is fully inserted into the distal end of the adapter.

As with the aforementioned mouth piece, the proximal end of the mouth piece adapter may be of expanded external diameter as compared to the distal open end to provide a comfortable interface with a user's lips.

It will be understood that the mouth piece adapter is multi-functional, enabling connection not only to a vocal training device according to the present invention, but also to other such training devices, and in some uses allows users to fully articulate whilst still benefiting from the SOVT effects. For example, the mouth piece adapter may be used to couple an SOVT straw to a voice mask. Voice masks may be used to form a seal against a user's face around their mouth for enabling full articulation. Typically, the mask is shaped to create a chamber over the mouth which funnels into a narrow outlet. The mouth piece adapter of the present invention can be fitted to the outlet of the mask, and then the device according to the present invention, or another SOVT straw, can be coupled to the adapter.

Essentially, the mouth piece adapter provides a connected system of mouth to mask to mouth piece to SOVT straw to atmosphere.

Examples according to the present invention will now be described with reference to the accompanying Figures, in which.

Figure 1:
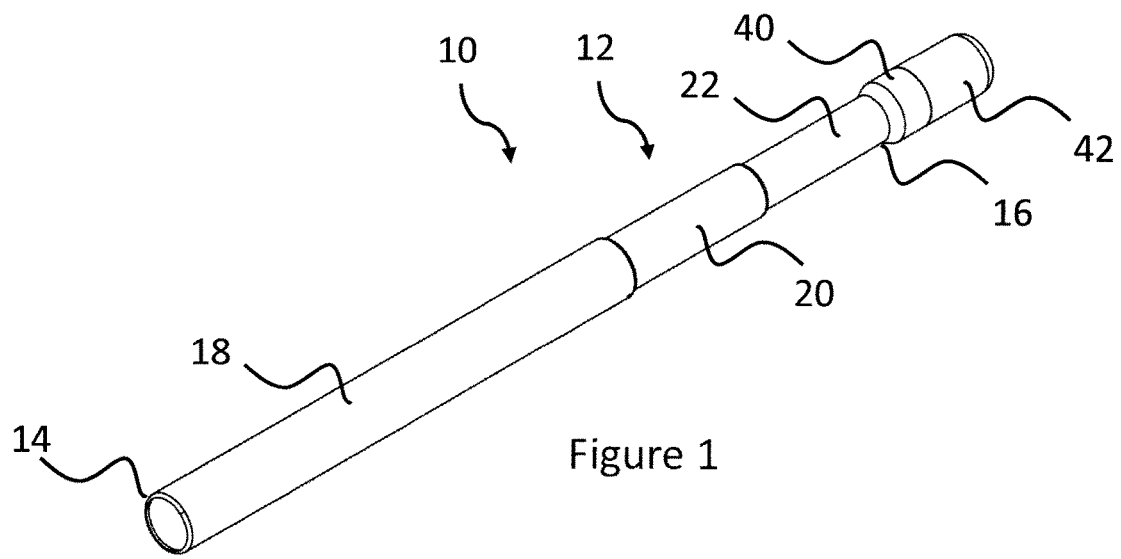
FIG. 1 is an isometric view of a vocal training device according to a first embodiment of the present invention.
Figure 2:
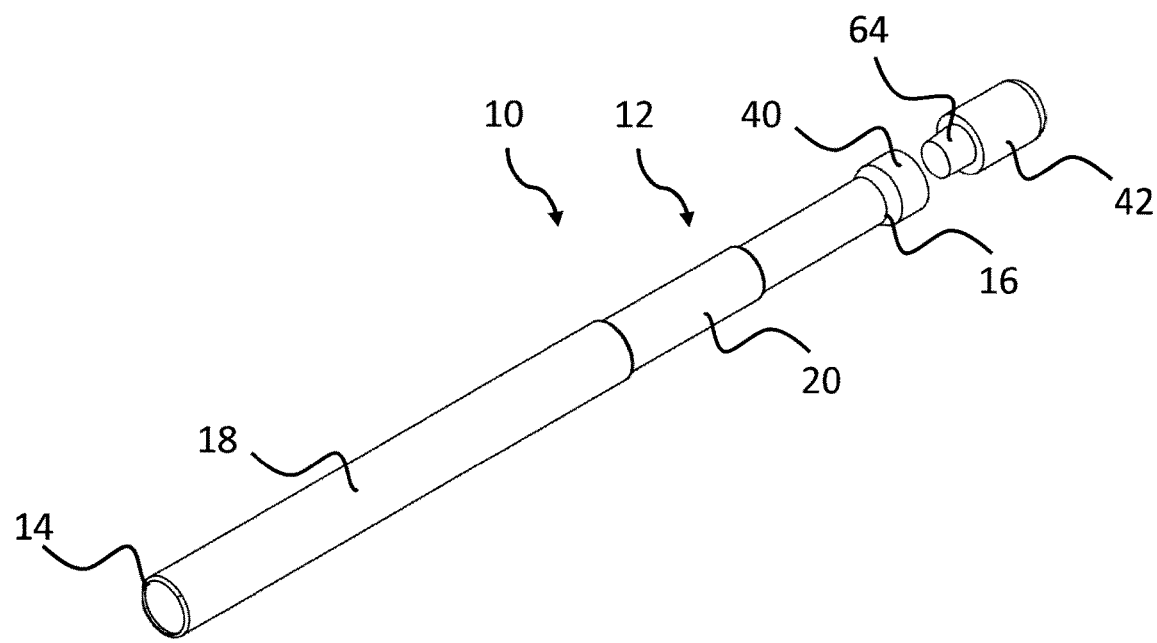
FIG. 2 is a partially exploded isometric view of the vocal training device of FIG. 1.
Figure 3:
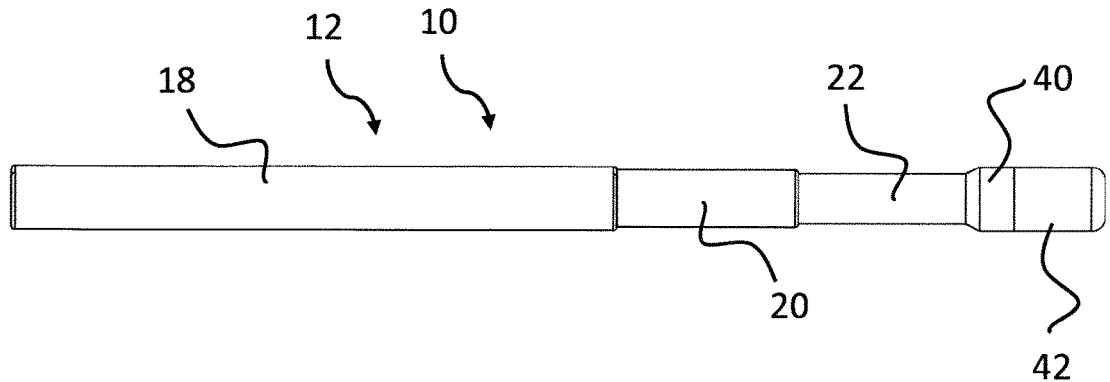
FIG. 3 is a plan view of the vocal training device of FIG. 1.

Referring to FIGS. 1 to 9, a first embodiment of a vocal training device 10 according to the present invention is shown.

The vocal training device 10 has a generally cylindrical hollow body 12. The generally cylindrical hollow body 12 comprises a first end 14 and a second end 16. Each of the first end 14 and the second end 16 are open.

The generally cylindrical hollow body 12 also comprises a first tube member 18, a second tube member 20 and a third tube member 22.

Figure 4:
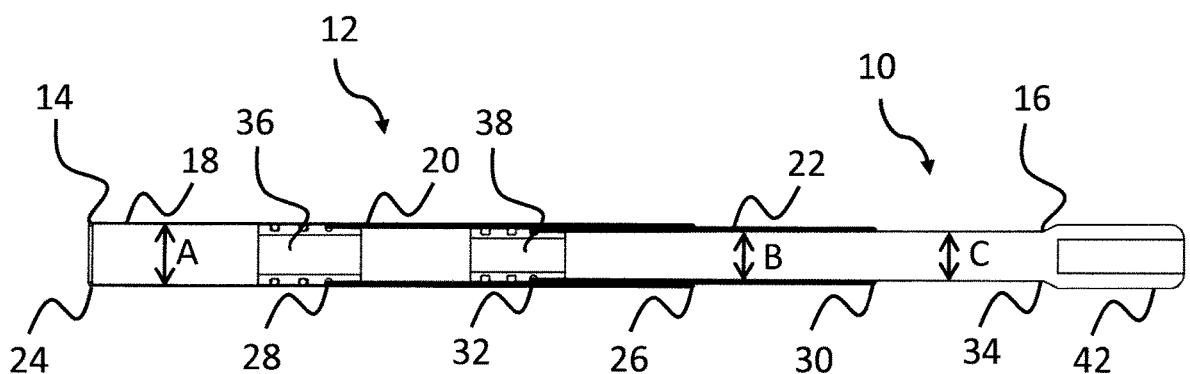
FIG. 4 is a section view of the vocal training device of FIG. 1.
Figure 5:
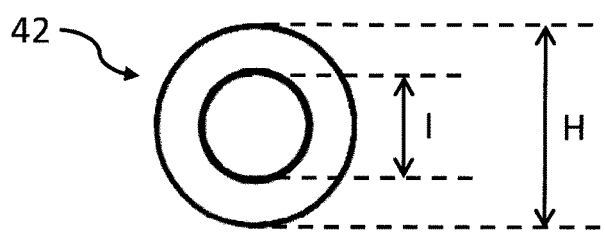
FIG. 5 is an alternative section view of the vocal training device of FIG. 1.

With particular reference to FIG. 4, the first tube member 18 has a first end 24 and a second end 26. Each of the first end 24 and the second end 26 of the first tube member 18 is open. The first tube member also has an internal diameter A.

The second tube member 20 has a first end 28 and a second end 30. Each of the first end 28 and the second end 30 of the second tube member 20 is open. The second tube member has an internal diameter B.

Similarly, the third tube member 22 has a first end 32 and a second end 34. Each of the first end 32 and the second end 34 of the third tube member 22 is open. The third tube member has an internal diameter C.

The internal diameter A of the first tube member 18 is greater than the internal diameter B of the second tube member 20 and the internal diameter C of the third tube member 22.

The internal diameter B of the second tube member 20 is greater than the internal diameter C of the third tube member 22.

In some examples of the first embodiment, the internal diameter A of the first tube member 18 may be 0.9 cm, the internal diameter B of the second tube member 20 may be 0.8 cm and the internal diameter C of the third tube member 22 may be 0.7 cm.

The generally cylindrical hollow body 12 also has a first telescopic connector 36 and a second telescopic connector 38, as will be described further below.

The vocal training device 10 also includes a connector 40 and a vocal training attachment member 42.

Figure 7:
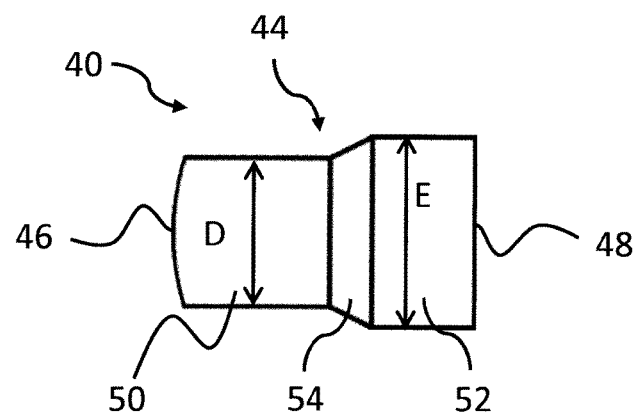
FIG. 7 is a plan view of a connector for use with the vocal training device of FIG. 1.
Figure 8:
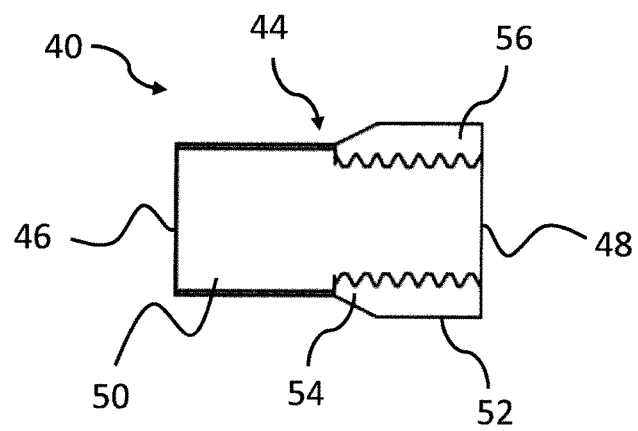
FIG. 8 is a section view of the connector of FIG. 7.

With particular reference to FIGS. 7 and 8, the connector 40 comprises a cylindrical hollow body 44 having a first end 46 and a second end 48. Each of the first end 46 and the second end 48 is open.

The connector 40 has a first portion 50 that is adjacent to the first end 46 and has an outer diameter D. The connector 40 has a second portion 52 that is adjacent to the second end 48 and has an outer diameter E.

In some examples of the invention, the outer diameter D of the first portion 50 of the connector 40 may be 0.7 cm and the outer diameter E of the second portion 52 of the connector 40 may be 0.9 cm.

An intermediate portion 54 is provided between the first portion 50 and the second portion 52 such that the second portion 52 is flared relative to the first portion 50. The outer diameter E of the second portion 52 is therefore greater than the outer diameter D of the first portion 50.

The connector 40 also includes an internal attachment member 56 in the form of a screw thread.

Figure 9:
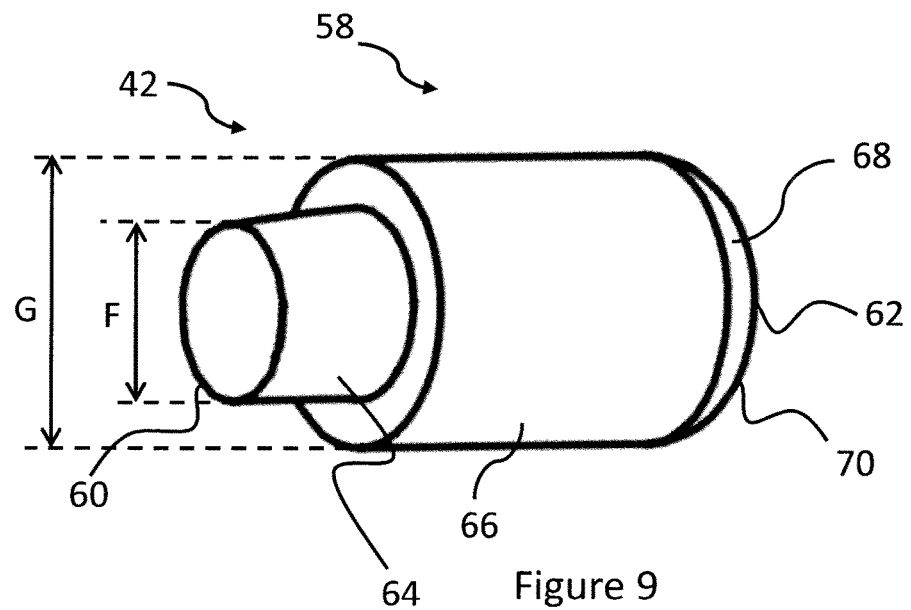
FIG. 9 is an isometric view of a vocal training attachment member for use with the vocal training device of FIG. 1.

With particular reference to FIG. 9, the vocal training attachment member 42 has a generally cylindrical hollow body 58 having a first end 60 and a second end 62. Each of the first end 60 and the second end 62 of the generally cylindrical body 58 is open. The generally cylindrical body 58 of the vocal training attachment member 42 has a first body portion 64, a second body portion 66 and a third body portion 68.

The first body portion 64 of the vocal training attachment member 42 has an outer diameter F. The second body portion 66 of the vocal training attachment member 42 has an outer diameter G. The outer diameter G of the second body portion 66 of the vocal training attachment member 42 is greater than the outer diameter F of the first body portion 64 of the vocal training attachment member 42.

In some examples of the first embodiment, the outer diameter F of the first body portion 64 of the vocal training attachment member 42 may be 0.6 cm and the outer diameter G of the body portion 66 of the vocal training attachment member 42 may be 0.9 cm.

The outer diameter G of the second body portion 66 of the vocal training attachment member 42 is substantially equal to the outer diameter E of the second portion 52 of the connector 40. The third body portion 68 of the vocal training attachment member has a sloping outer wall 70 such that the outer diameter H of the second end 62 of the vocal training attachment member 42 is less than the diameter G of the second body portion 66 of the vocal training attachment member 42.

In some examples of the invention, the outer diameter H of the second end 62 of the vocal training attachment member 42 may be 0.6 mm.

At the second end 62 of the vocal training attachment member 42, the internal diameter I of the vocal training attachment member 42 is less than the internal diameter A of the first tube member 18. In some examples of the first embodiment, the internal diameter I at the second end 62 of the vocal training attachment member 42 may be 0.5 cm. In other examples of the first embodiment, the internal diameter I at the second end 62 of the vocal training attachment member 42 may be 0.3 cm.

The vocal training attachment member 42 of the first embodiment of the invention is an aperture reducing attachment.

A user can select a vocal training attachment member 42 having an internal diameter that provides the desired resistance for vocal training exercises according to their physiology.

The vocal training device 10 is manufactured and assembled as follows.

Each of the first tube member 18, the second tube member 20, the third tube member 22, the first telescopic connector 36, the second telescopic connector 38, the connector 40 and the vocal training attachment member 42 is manufactured from a suitable reusable material, for example a metal such as stainless steel.

In some examples of the invention, the stainless steel may be an austenitic grade stainless steel, such as stainless steel 304, for example food grade stainless steel.

The first telescopic connector 36 is installed within the hollow interior of the first tube member 18. A first 'O' ring (not shown) is placed at either end of the first telescopic connector 36. Similarly, the second telescopic connector 38 is installed within the hollow interior of the second tube member 20. A second 'O' ring (not shown) is placed at either end of the first telescopic connector 36.

The first end 28 of the second tube member 20 is positioned within the second end 26 of the first tube member 18 such that the outer wall of the second tube member 20 engages an 'O' ring of the first telescopic connector 36. The second tube member 20 can thus be slidably moved within the hollow interior of the first tube member 18.

The first end 32 of the third tube member 22 is positioned within the second end 30 of the second tube member 20 such that the third tube member 22 engages an 'O' ring of the second telescopic connector 38. The third tube member 22 can thus be slidably moved within the hollow interior the second tube member 20.

Figure 6:
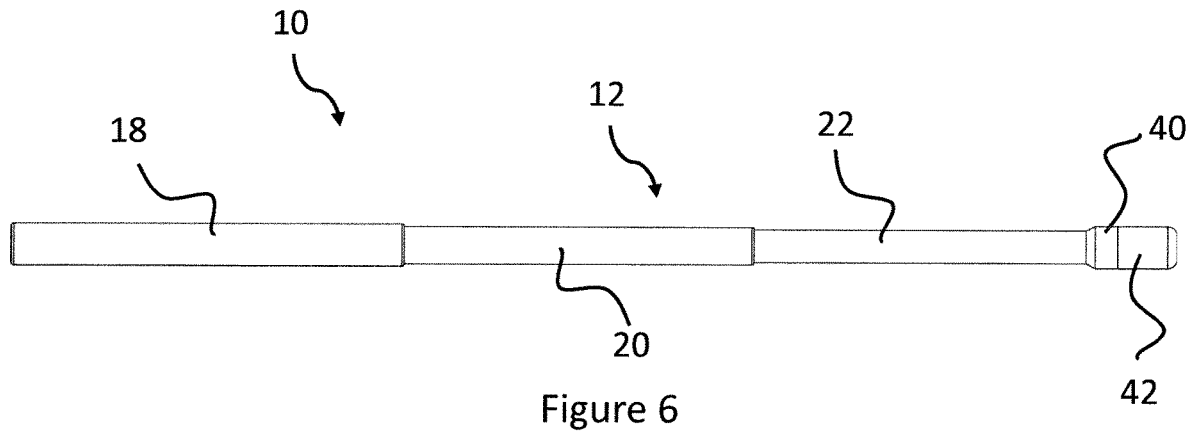
FIG. 6 is a plan view of the vocal training device of FIG. 1 in an expanded position.

The vocal training device 10 can, therefore, be moved between a compact configuration (in which the third tube member 22 is positioned fully within the second tube member 20 and the second tube member 20 is positioned fully within the first tube member 18) and an extended configuration (as shown in FIG. 6, in which the second tube member 20 extends from the second end 26 of the first tube member 18 and the third tube member 22 extends from the second end 30 of the second tube member 20).

It will be understood that, in the compact configuration, the second end 26 of the first tube member 18, the second end 30 of the second tube member 20 and the second end 34 of the third tube member 22 are co-located with the second end 16 of the generally cylindrical hollow body 12.

In the extended configuration, only the second end 34 of the third tube member 22 is co-located with the second end 16 of the generally cylindrical hollow body 12.

In a configuration that is intermediate the compact configuration and the extended configuration, the 'intermediate configuration', the second end 30 of the second tube member 20 and the second end 34 of the third tube member 22 are co-located with the second end 16 of the generally cylindrical hollow body 12.

The generally cylindrical hollow body 12 can thus have three different lengths, according to the positions of the telescopic first, second and third tube members 18, 20, 22.

The first end 46 of the connector 40 is positioned within the second end 34 of the third tube member 22 such that the intermediate portion 54 of the connector 40 abuts the second end 34 of the third tube member 22. The connector 40 is held in place within the third tube member 22 by any suitable fastening means, for example a push-fit fastening or a screw thread fastening.

The vocal training attachment member 42 is then fastened to the connector 40 by inserting the first body portion 64 of the vocal training attachment member 42 within the second flared portion 52 of the connector 40. The vocal training attachment member 42 is held in place within the second portion 52 of the connector 40 by any suitable fastening means, for example a push-fit fastening or a screw thread fastening (as shown in FIG. 8).

Since each of the first tube member 18, the second tube member 20, the third tube member 22, the connector 40 and the vocal training attachment member 42 are open at each end, the vocal training device 10 is a hollow tube or cylinder or pipe and thus air (or any other fluid or flowable, low viscosity, substance) can be drawn from the second end 62 of the vocal training attachment member 42 to the first end 24 of the first tube member 18 (which is co-located with the first end 14 of the generally cylindrical hollow body 12 of the vocal training device 10). Similarly, air (or any other fluid or flowable, low viscosity, substance) can be drawn from the first end 24 of the first tube member 18 to the second end 62 of the vocal training attachment member 42. In other words, the vocal training device 10 is a straw-like device.

The 'O' rings ensure that the joints between the first, second and third tube members 18, 20, 22 are sealed to prevent the escape of air, water or other fluid from the joints.

Use of the vocal training device 10 for vocal training exercises will now be described.

The telescopic arrangement of the first, second and third tube members 18, 20, 22 allows the resistance of the vocal training device to be easily adjusted according to a user's requirements. The length of the device in concert with the airflow direction will dictate the resistance offered. As the device expands in diameter across its length, the more resistance it will have, whereas, as the device contracts in diameter across its length, the less resistance it will have. Therefore, users can manipulate the total length and airflow direction to increase or decrease the resistance as desired.

Therefore, to increase the resistance, a user can place the vocal training device 10 in its extended configuration (as shown in FIG. 6, and in which the second tube member 20 extends from the second end 26 of the first tube member 18 and the third tube member 22 extends from the second end 30 of the second tube member 20).

In order to reduce the resistance, a user can place the vocal training device 10 in its compact configuration (in which the third tube member 22 is positioned fully within the second tube member 20 and the second tube member 20 is positioned fully within the first tube member 18).

The resistance achieved can clearly be optimised according to a user's requirements by varying the position of the second tube member 20 relative to the first tube member 18 and/or by varying the position of the third tube member 22 relative to the second tube member 20. In one exemplary arrangement, the third tube member 22 may be fully contracted within the second tube member 20 and the second tube member 20 may be fully extended relative to the first tube member 18.

A user is also able to adjust the resistance by taking advantage of the differences between the internal diameter A at the first end 14 of the generally cylindrical hollow body 12 and the internal diameter I at the second end 62 of the vocal training attachment member 42.

As the diameter of the body decreases along its length, the pressure increases. This means that there will be more resistance within the device. This means that if a user blows through the device from the first open end 14 of the generally cylindrical hollow body 12 (the widest end) to the second open end 62 of the vocal training attachment member 42 (the narrowest end), there will be a greater resistance. This will give a "harder" vocal workout. In contrast, if the user reverses the device (and thus the flow direction through it), i.e., blowing from the second open end 62 of the vocal training attachment member 42 to the first open end 14 of the generally cylindrical hollow body 12, then the resistance will decrease thereby giving an "easier" vocal workout.

For a vocal training device 10 having a particular vocal training attachment member 42, at least twelve different resistances can be achieved simply by varying the length of the generally cylindrical hollow body 12 (by varying the relative positions of the first, second and third telescopic tube members 18, 20, 22) and by varying the orientation of the vocal training device 10 (i.e. whether the user blows into the first end 14 of the generally cylindrical hollow body 12 or into the second end 62 of the vocal training attachment member 42). The resistance achieved can also be varied by using a vocal training attachment member 42 having a different internal diameter.

Three different resistances can be achieved by positioning the first end 14 of the hollow body 12 of the vocal training device 10 in a user's mouth and moving the first, second and third tube members 18, 20, 22 between (1) the compact configuration, (2) the intermediate configuration and (3) the extended configuration.

Three further resistances can be achieved by positioning the second end 48 of the connector 40 in a user's mouth and moving the first, second and third tube members 18, 20, 22 between (1) the compact configuration, (2) the intermediate configuration and (3) the extended configuration.

Six additional resistances can be achieved by using a first vocal training attachment member 42 having one internal diameter I (say 0.5 cm) and six additional resistances can be achieved by using a second vocal training attachment member 42 having an alternative internal diameter I (say 0.3 cm).

The vocal training device 10 is thus advantageous as it is versatile, yet less complex than other variable resistance SOVT training devices.

Features of the vocal training device described hereinafter with reference to the second to eighth embodiments which are common to the vocal training device 10 according to the first embodiment are identified with reference numbers that are 100×, 200×, 300×, etc greater than the reference numbers used for the features of the vocal training device 10.

A second embodiment of the present invention will now be described with reference to FIGS. 10 to 14.

The vocal training device 110 of the second embodiment has a generally cylindrical hollow body 112. The generally cylindrical hollow body 112 comprises a first end 114 and a second end 116. Each of the first end 114 and the second end 116 are open.

The generally cylindrical hollow body 112 also comprises a first tube member 118, a second tube member 120 and a third tube member 122.

Figure 12:
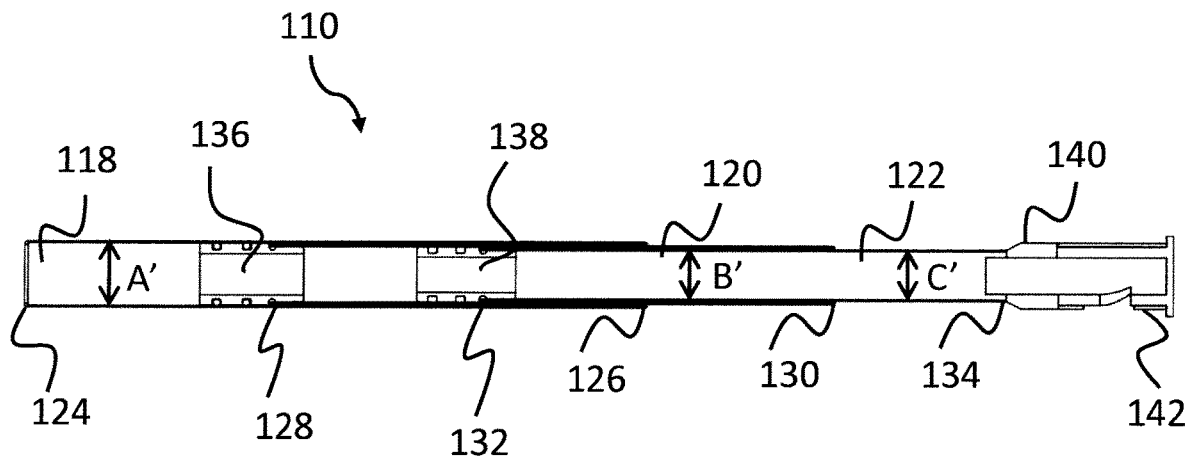
FIG. 12 is a section view of the vocal training device of FIG. 10.

With particular reference to FIG. 12, the first tube member 118 has a first end 124 and a second end 126. Each of the first end 124 and the second end 126 of the first tube member 118 is open. The first tube member also has an internal diameter A'.

The second tube member 120 has a first end 128 and a second end 130. Each of the first end 128 and the second end 130 of the second tube member 120 is open. The second tube member has an internal diameter B'.

Similarly, the third tube member 122 has a first end 132 and a second end 134. Each of the first end 132 and the second end 134 of the third tube member 122 is open. The third tube member has an internal diameter C'.

The internal diameter A' of the first tube member 118 is greater than the internal diameter B' of the second tube member 120 and the internal diameter C' of the third tube member 122.

The internal diameter B' of the second tube member 120 is greater than the internal diameter C' of the third tube member 122.

In some examples of the present invention, the internal diameter A' of the first tube member 118 may be 0.9 cm, the internal diameter B' of the second tube member 120 may be 0.8 cm and the internal diameter C' of the third tube member 122 may be 0.7 cm.

The generally cylindrical hollow body 112 also has a first telescopic connector 136 and a second telescopic connector 138, as will be described further below.

The vocal training device 110 also includes a connector 140 and a vocal training attachment member 142.

The connector 140 is like the connector 40 of the first embodiment and so will not be described further. Features of the connector 140 which are common with the connector 40 of the first embodiment are identified with reference numbers 100 greater than the reference numbers used for the features of the connector 40.

Figure 10:
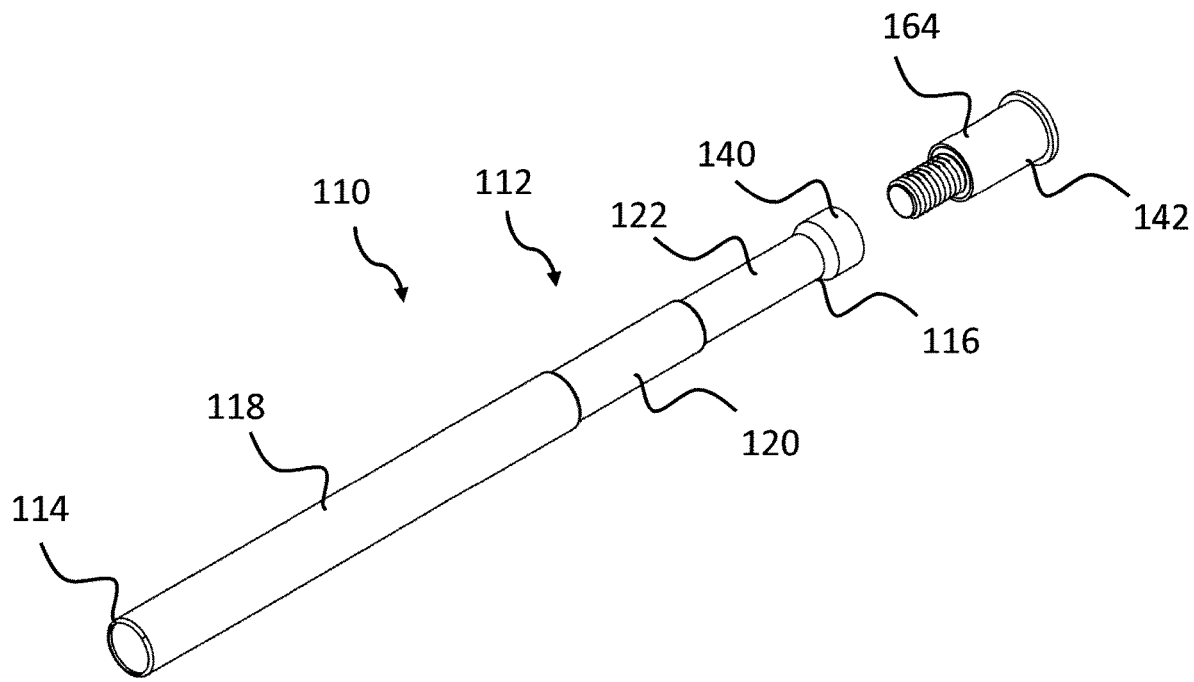
FIG. 10 is a partially exploded isometric view of a vocal training device according to a second embodiment of the present invention.
Figure 11:
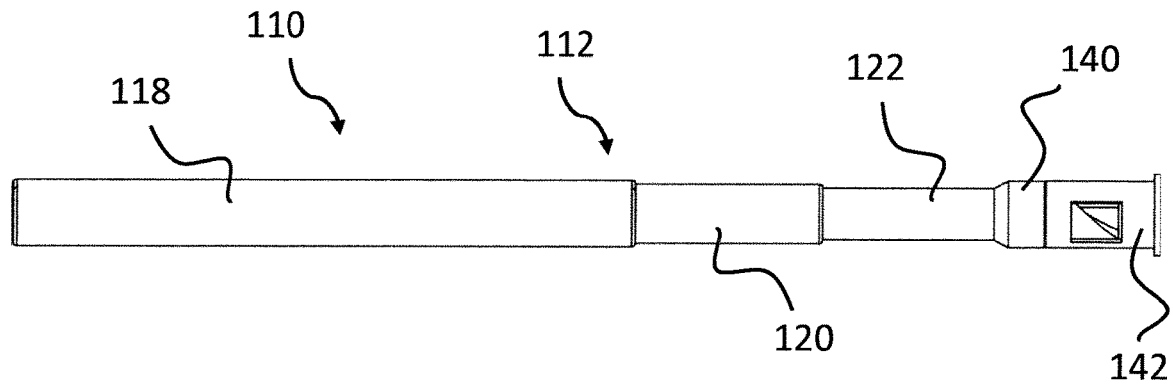
FIG. 11 is a plan view of the vocal training device of FIG. 10.
Figure 13:
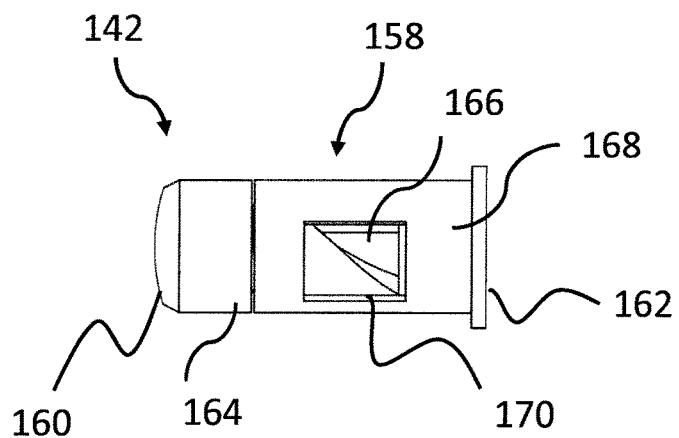
FIG. 13 is a plan view of a vocal training attachment member for use with the vocal training device of FIG. 10.
Figure 14:
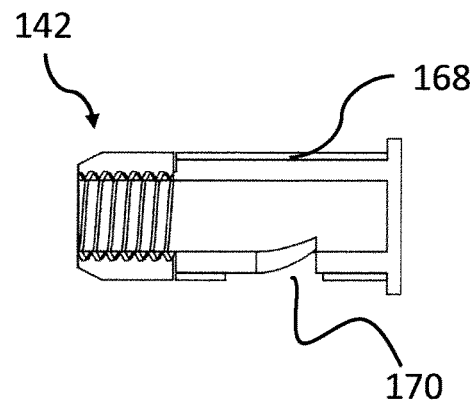
FIG. 14 is a section view of the vocal training attachment member of FIG. 13.
Figure 15:
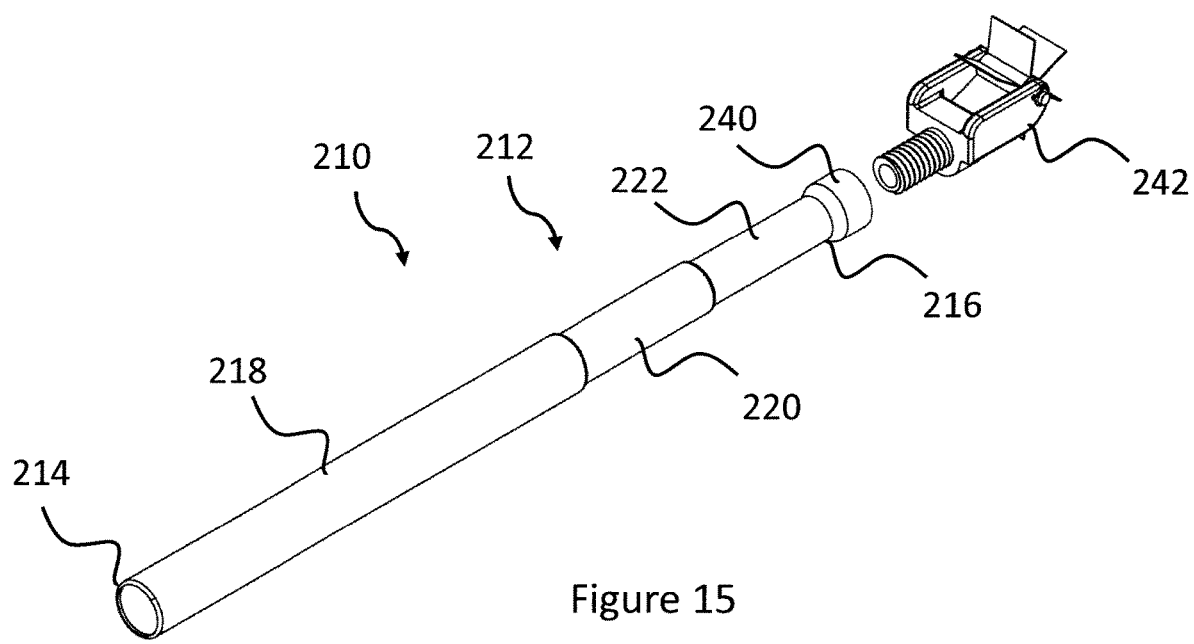
FIG. 15 is a partially exploded isometric view of a vocal training device according to a third embodiment of the present invention.
Figure 16:
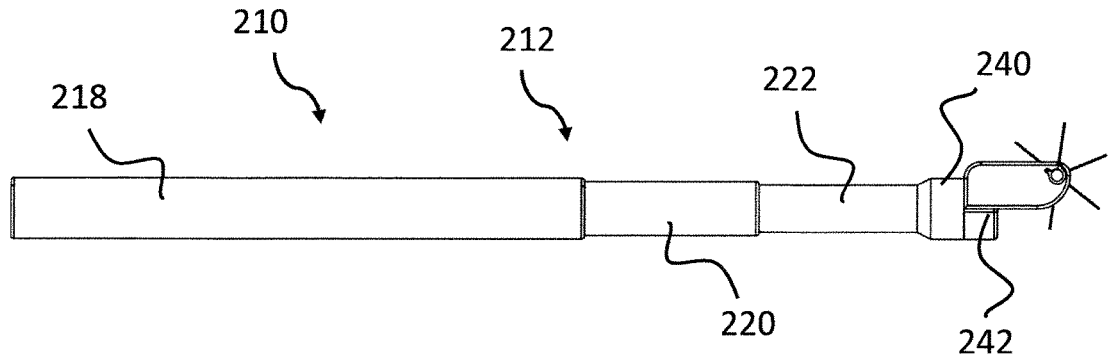
FIG. 16 is a plan view of the vocal training device of FIG. 15.

Referring now to FIGS. 10, 13 and 14, the vocal training attachment member 142 has a generally cylindrical hollow body 158 having a first end 160 and a second end 162. Each of the first end 160 and the second end 162 of the generally cylindrical body 158 is open. The generally cylindrical hollow body 158 has an outer wall 164 in which a triangular slot 166 is formed. The triangular slot 166 extends through the outer wall 164 to the interior of the hollow body 158.

The generally cylindrical hollow body 158 also has an outer sleeve 168 which extends around the outer wall 164 of the generally cylindrical hollow body 158. The outer sleeve 168 includes a generally rectangular opening 170. The outer sleeve 168 is rotatably mounted on the generally cylindrical hollow body 158 such that the position of the generally rectangular opening 170 relative to the triangular slot 166 can be changed. In this way, the size of the opening in the outer wall 164 of the hollow body 158 can be increased or decreased by a user.

The vocal training attachment member 142 of the second embodiment of the invention is, therefore, a variable aperture reducing attachment.

A user can adjust the resistance provided by the vocal training device 110 for vocal training exercises according to their physiology using the variable aperture reducing attachment 142 as will be described below.

The vocal training device 110 is manufactured and assembled as follows.

Each of the first tube member 118, the second tube member 120, the third tube member 122, the first telescopic connector 136, the second telescopic connector 138, the connector 140 and the vocal training attachment member 142 is manufactured from a suitable reusable material, for example a metal such as stainless steel.

In some examples of the invention, the stainless steel may be an austenitic grade stainless steel, such as stainless steel 304, for example food grade stainless steel.

The first telescopic connector 136 is installed within the hollow interior of the first tube member 118. A first 'O' ring (not shown) is placed at either end of the first telescopic connector 136. Similarly, the second telescopic connector 138 is installed within the hollow interior of the second tube member 120. A second 'O' ring (not shown) is placed at either end of the second telescopic connector 138.

The first end 128 of the second tube member 120 is positioned within the second end 126 of the first tube member 118 such that the outer wall of the second tube member 120 engages an 'O' ring of the first telescopic connector 136. The second tube member 120 can thus be slidably moved within the hollow interior of the first tube member 118.

The first end 132 of the third tube member 122 is positioned within the second end 130 of the second tube member 120 such that the third tube member 122 engages an 'O' ring of the second telescopic connector 138. The third tube member 122 can thus be slidably moved within the hollow interior the second tube member 120.

The vocal training device 110 can, therefore, be moved between a compact configuration (in which the third tube member 122 is positioned fully within the second tube member 120 and the second tube member 120 is positioned fully within the first tube member 118) and an extended configuration (in which the second tube member 120 extends from the second end 126 of the first tube member 118 and the third tube member 122 extends from the second end 130 of the second tube member 120).

It will be understood that, in the compact configuration, the second end 126 of the first tube member 118, the second end 130 of the second tube member 120 and the second end 134 of the third tube member 122 are co-located with the second end 116 of the generally cylindrical hollow body 112.

In the extended configuration, only the second end 134 of the third tube member 122 is co-located with the second end 116 of the generally cylindrical hollow body 112.

In a configuration that is intermediate the compact configuration and the extended configuration, the 'intermediate configuration', the second end 130 of the second tube member 120 and the second end 134 of the third tube member 122 are co-located with the second end 116 of the generally cylindrical hollow body 112.

The generally cylindrical hollow body 112 can thus have three different lengths, according to the positions of the telescopic first, second and third tube members 118, 120, 122.

The first end 146 of the connector 140 is positioned within the second end 134 of the third tube member 122 such that the intermediate portion 154 of the connector 140 abuts the second end 134 of the third tube member 122. The connector 140 is held in place within the third tube member 122 by any suitable fastening means, for example a push-fit fastening or a screw thread fastening.

The vocal training attachment member 142 is then fastened to the connector 140 by inserting the first end 160 of the vocal training attachment member 142 within the second flared portion 152 of the connector 140. The vocal training attachment member 142 is held in place within the second portion 152 of the connector 140 by any suitable fastening means, for example a push-fit fastening or a screw thread fastening.

Since each of the first tube member 118, the second tube member 120, the third tube member 122, the connector 140 and the vocal training attachment member 142 are open at each end, the vocal training device 110 is a hollow tube or cylinder or pipe and thus air (or any other fluid or flowable, low viscosity, substance) can be drawn from the second end 162 of the vocal training attachment member 142 to the first end 124 of the first tube member 118 (which is co-located with the first end 114 of the generally cylindrical hollow body 112 of the vocal training device 110). Similarly, air (or any other fluid or flowable, low viscosity, substance) can be drawn from the first end 124 of the first tube member 118 to the second end 162 of the vocal training attachment member 142. In other words, the vocal training device 110 is a straw-like device.

The 'O' rings ensure that the joints between the first, second and third tube members 118, 120, 122 are sealed to prevent the escape of air, water or other fluid from the joints.

Use of the vocal training device 110 for vocal training exercises will now be described.

As described in relation to the first embodiment, the telescopic arrangement of the first, second and third tube members 118, 120, 122 allows the resistance of the vocal training device 110 to be easily adjusted according to a user's requirements. The longer the length of the device 110, the greater the resistance it will have. In contrast, the shorter the length of the device 110, the less resistance it will have.

Therefore, to increase the resistance, a user can place the vocal training device 110 in its extended configuration (in which the second tube member 120 extends fully from the second end 126 of the first tube member 118 and the third tube member 122 extends fully from the second end 130 of the second tube member 120).

In order to reduce the resistance, a user can place the vocal training device 110 in its compact configuration (in which the third tube member 122 is positioned fully within the second tube member 120 and the second tube member 120 is positioned fully within the first tube member 118).

The resistance achieved can clearly be optimised according to a user's requirements by varying the position of the second tube member 120 relative to the first tube member 118 and/or by varying the position of the third tube member 122 relative to the second tube member 120, as described in relation to the first embodiment of the invention. In one exemplary arrangement (the intermediate configuration), the third tube member 122 may be fully contracted within the second tube member 120 and the second tube member 120 may be fully extended relative to the first tube member 118.

A user is also able to adjust the resistance by varying the position of the outer sleeve 168 on the variable aperture reducing attachment 142.

By closing the opening in the outer wall 164 of the variable aperture reducing attachment 142 with the outer sleeve 168, the pressure increases. This means that there will be more resistance within the device. This will give a "harder" vocal workout when a user breathes into the device 110. In contrast, if the user increases the size of the opening in the outer wall 164 by aligning the opening 170 with the slot 166, the resistance will decrease thereby giving an "easier" vocal workout.

For a vocal training device 110 having a variable aperture reducing attachment 142, different resistances can be achieved simply by varying the length of the generally cylindrical hollow body 112 (by varying the relative positions of the first, second and third telescopic tube members 118, 120, 122) and by varying the position of the sleeve 168 on the variable aperture reducing attachment 142 in order to change the size of the opening in the outer wall 164 of the variable aperture reducing attachment 142, thereby changing the resistance achieved.

The vocal training device 110 is thus advantageous as it is versatile, yet less complex than other variable resistance SOVT training devices.

A third embodiment of the present invention will now be described with reference to FIGS. 15 to 19.

The vocal training device 210 of the third embodiment has a generally cylindrical hollow body 212. The generally cylindrical hollow body 212 comprises a first end 214 and a second end 216. Each of the first end 214 and the second end 216 are open.

The generally cylindrical hollow body 212 also comprises a first tube member 218, a second tube member 220 and a third tube member 222.

Figure 17:
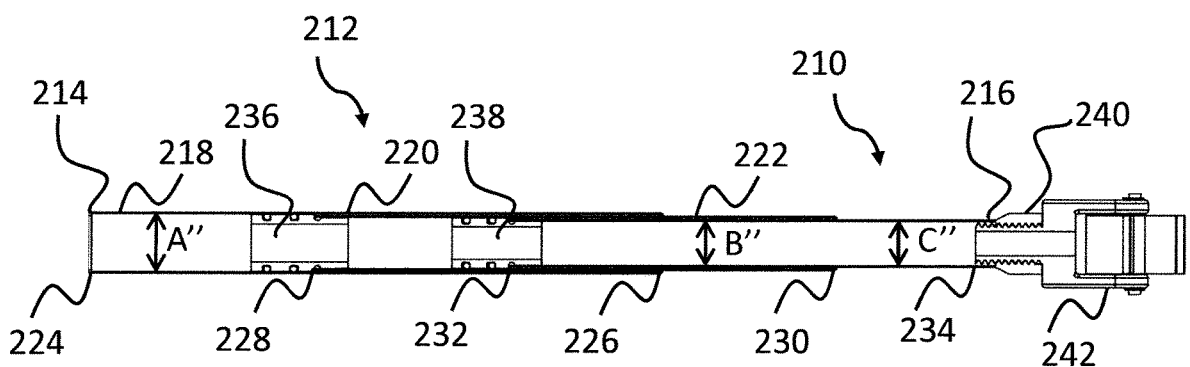
FIG. 17 is a section view of the vocal training device of FIG. 15.

With particular reference to FIG. 17, the first tube member 218 has a first end 224 and a second end 226. Each of the first end 224 and the second end 226 of the first tube member 218 is open. The first tube member also has an internal diameter A".

The second tube member 220 also has a first end 228 and a second end 230. Each of the first end 228 and the second end 230 of the second tube member 220 is open. The second tube member has an internal diameter B".

Similarly, the third tube member 222 has a first end 232 and a second end 234. Each of the first end 232 and the second end 234 of the third tube member 222 is open. The third tube member has an internal diameter C".

The internal diameter A" of the first tube member 218 is greater than the internal diameter B" of the second tube member 220 and the internal diameter C" of the third tube member 222.

The internal diameter B" of the second tube member 220 is greater than the internal diameter C" of the third tube member 222.

In some examples of the present invention, the internal diameter A" of the first tube member 218 may be 0.9 cm, the internal diameter B" of the second tube member 220 may be 0.8 cm and the internal diameter C" of the third tube member 222 may be 0.7 cm.

The generally cylindrical hollow body 212 also has a first telescopic connector 236 and a second telescopic connector 238, as will be described further below.

The vocal training device 210 also includes a connector 240 and a vocal training attachment member 242.

The connector 240 is like the connector 40 of the first embodiment and so will not be described further. Features of the connector 240 which are common with the connector 40 of the first embodiment are identified with reference numbers 200 greater than the reference numbers used for the features of the connector 40.

Figure 18:
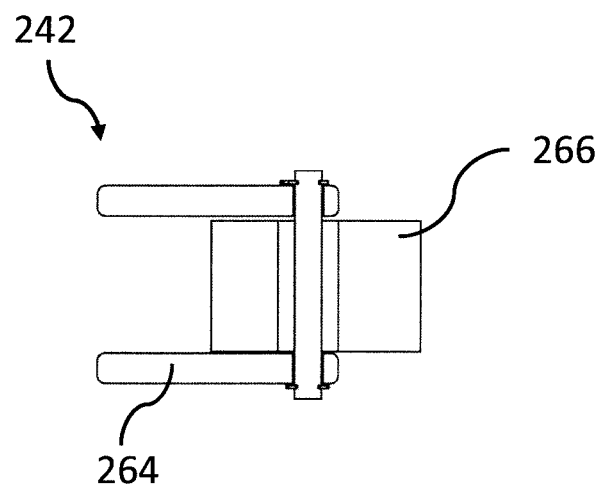
FIG. 18 is a plan view of a vocal training attachment member for use with the vocal training device of FIG. 15.
Figure 19:
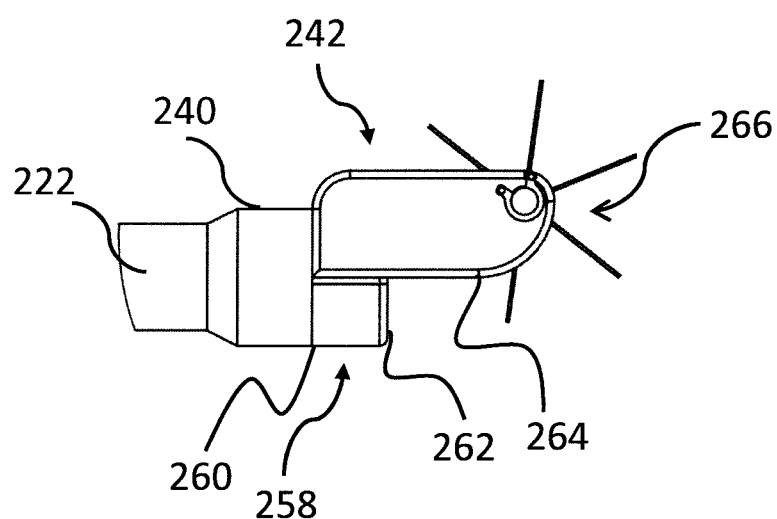
FIG. 19 is a section view of the vocal training attachment member of FIG. 15.
Figure 20:
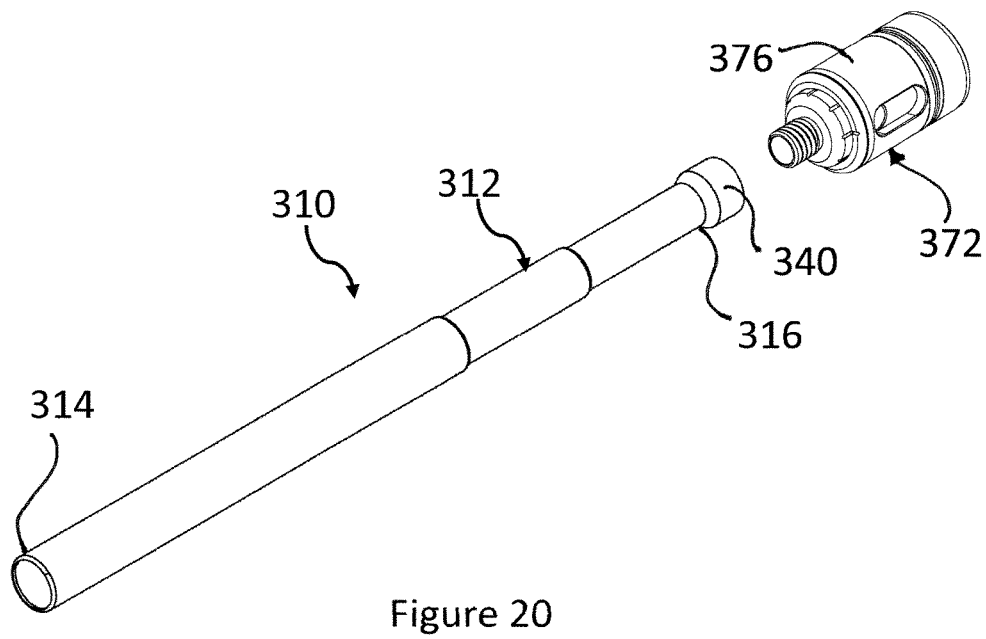
FIG. 20 is a partially exploded isometric view of a vocal training device according to a fourth embodiment of the present invention.
Figure 21:
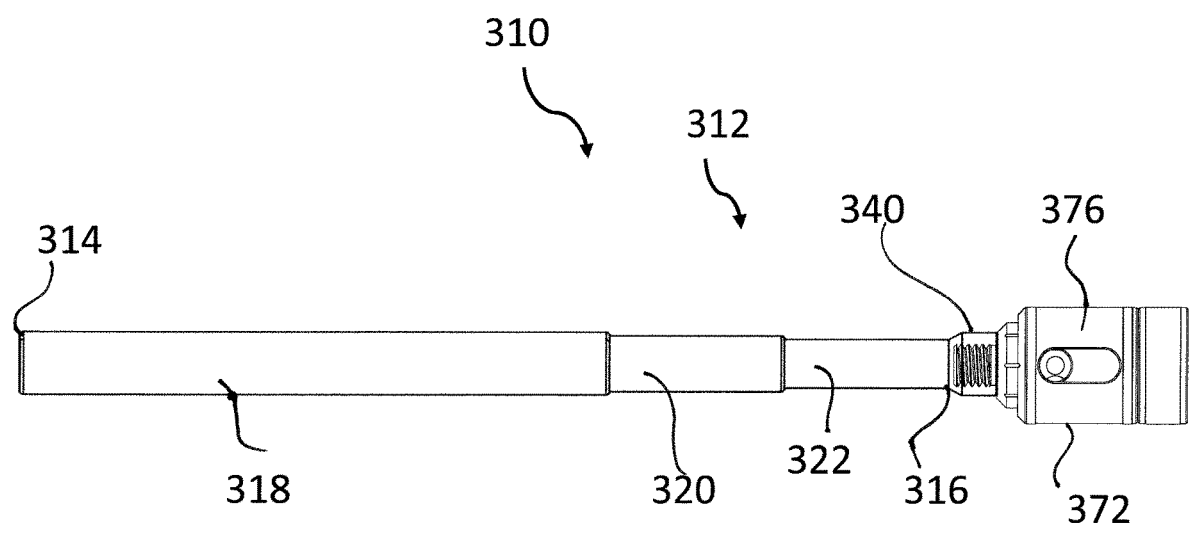
FIG. 21 is a plan view of the vocal training device of FIG. 20.
Figure 22:
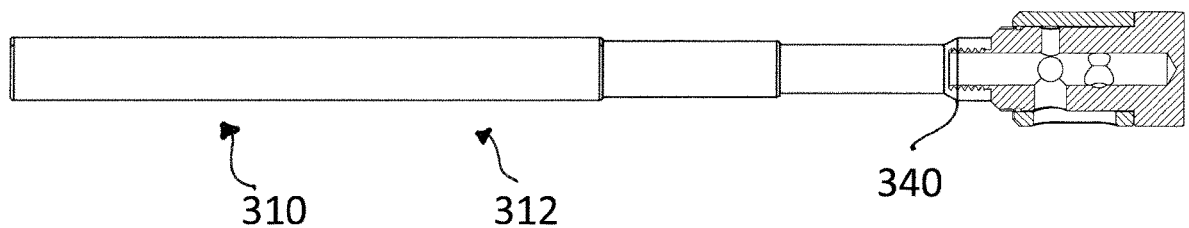
FIG. 22 is a section view of the vocal training device of FIG. 20.
Figure 23:
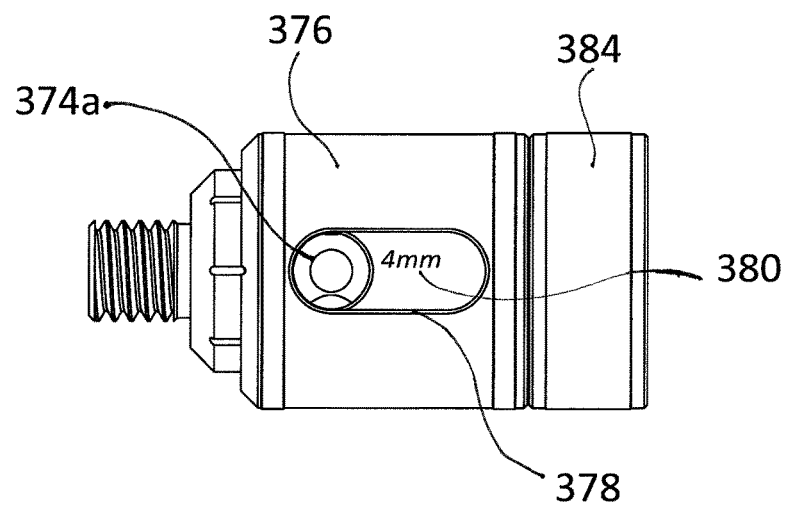
FIG. 23 is a plan view of a vocal training attachment member for use with the vocal training device of FIG. 20.
Figure 24:
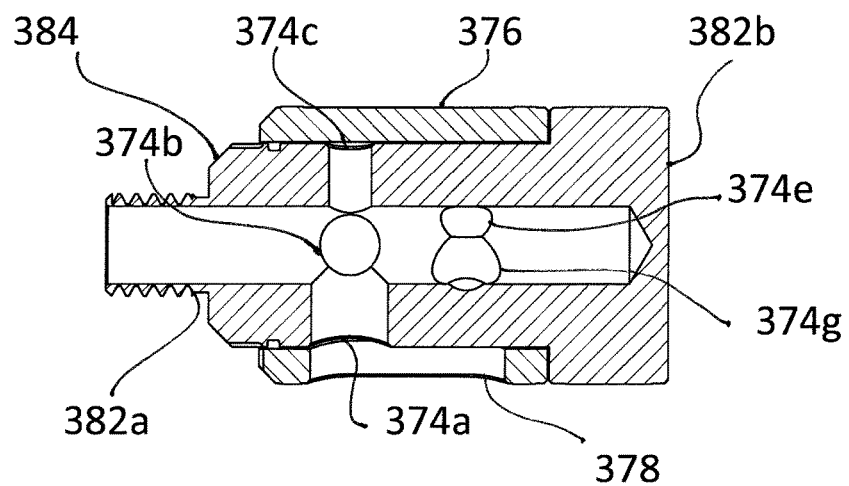
FIG. 24 is a section view of the vocal training attachment member of FIG. 23.
Figure 25:
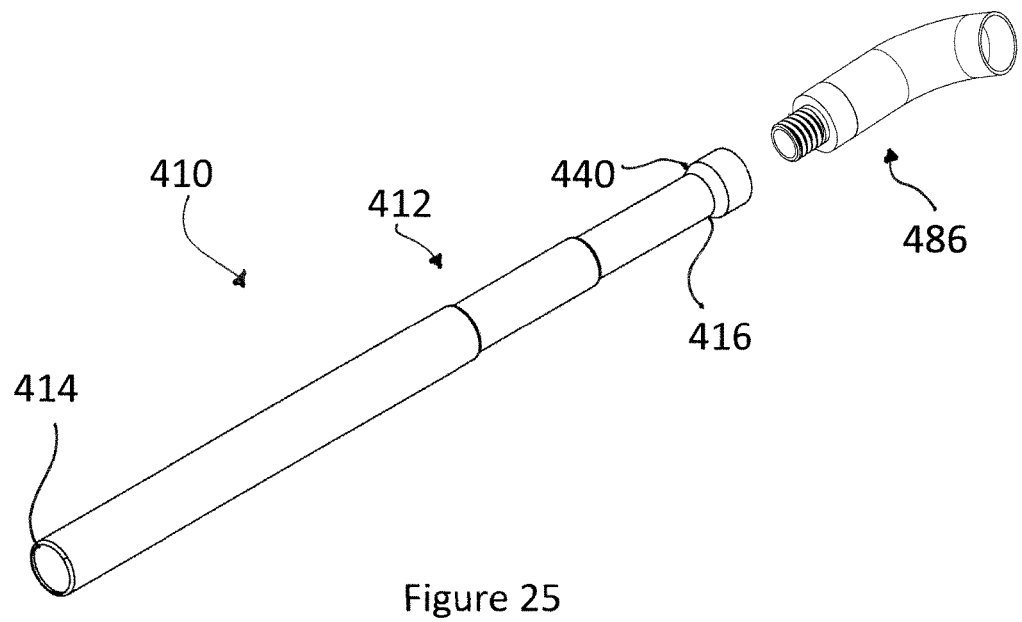
FIG. 25 is a partially exploded isometric view of a vocal training device according to a fifth embodiment of the present invention.
Figure 26:
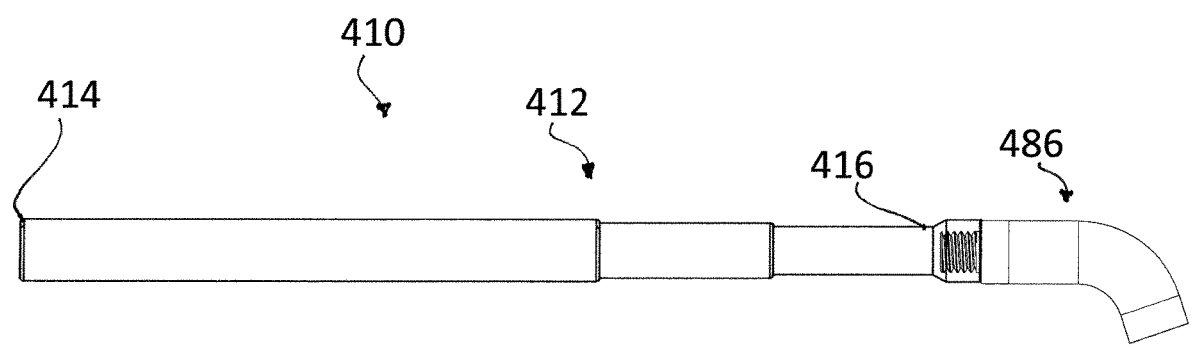
FIG. 26 is a plan view of the vocal training device of FIG. 25.
Figure 27:
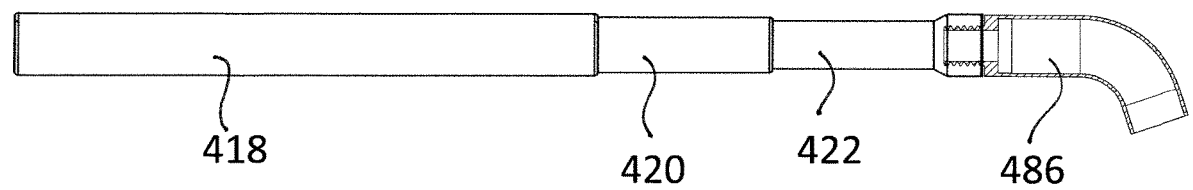
FIG. 27 is a section view of the vocal training device of FIG. 25.
Figure 28:
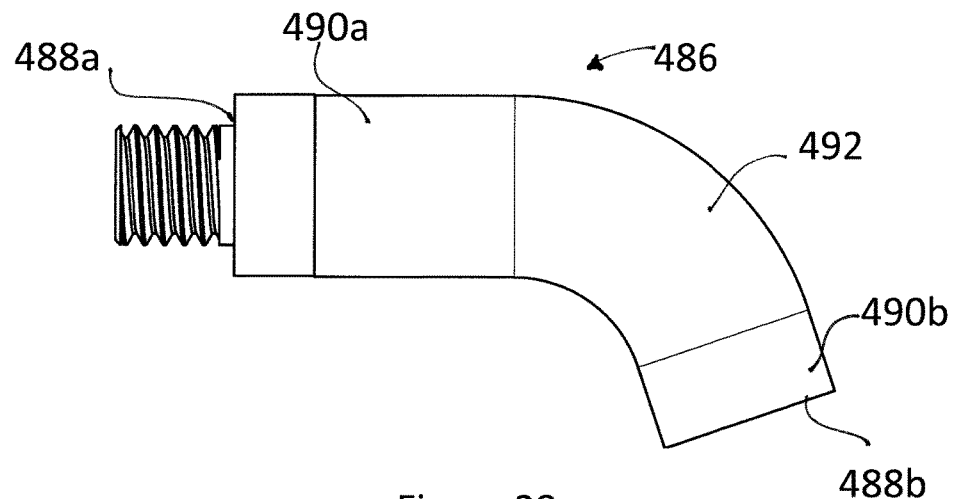
FIG. 28 is a plan view of a vocal training attachment member for use with the vocal training device of FIG. 25.
Figure 29:
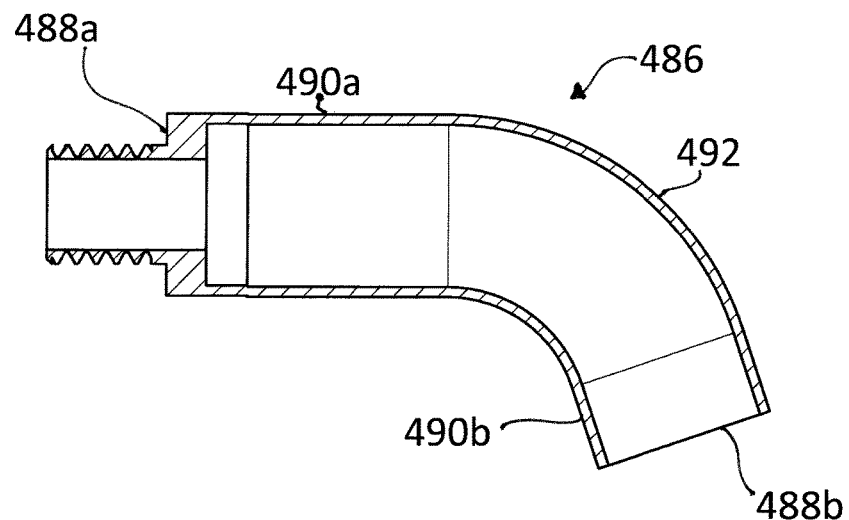
FIG. 29 is a section view of the vocal training attachment member of FIG. 28.
Figure 30:
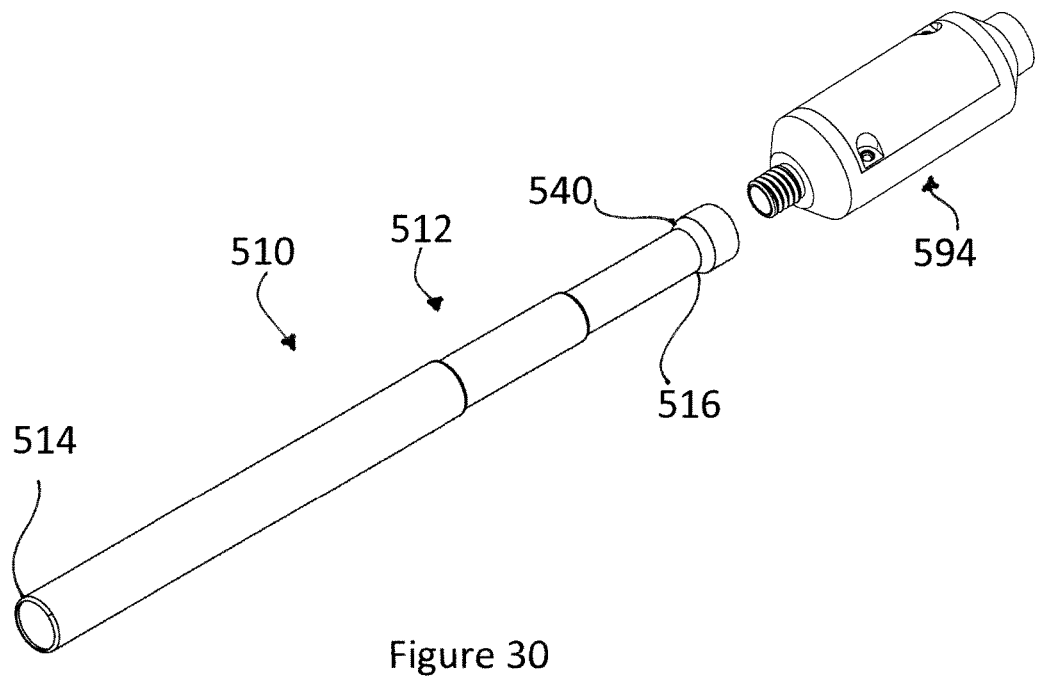
FIG. 30 is a partially exploded isometric view of a vocal training device according to a sixth embodiment of the present invention.
Figure 31:
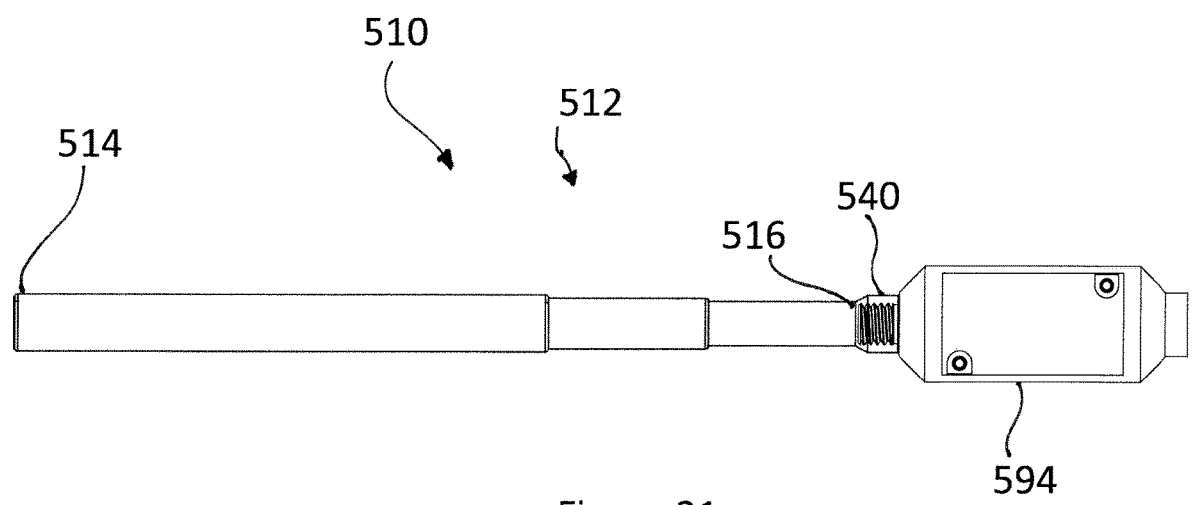
FIG. 31 is a plan view of the vocal training device of FIG. 30.
Figure 32:
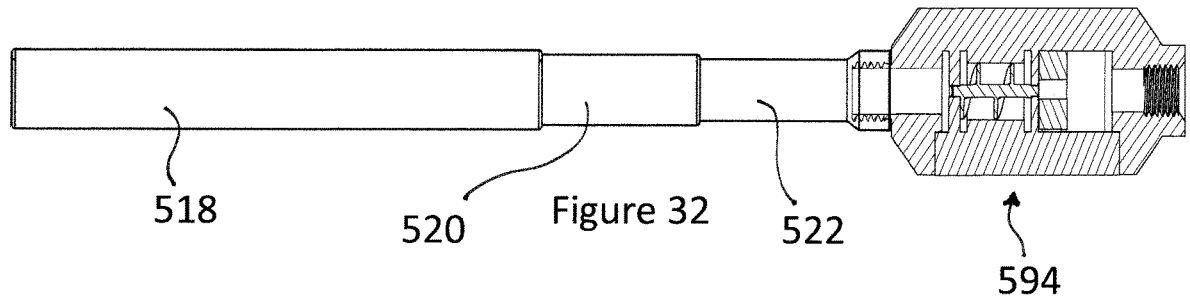
FIG. 32 is a section view of the vocal training device of FIG. 30.
Figure 33:
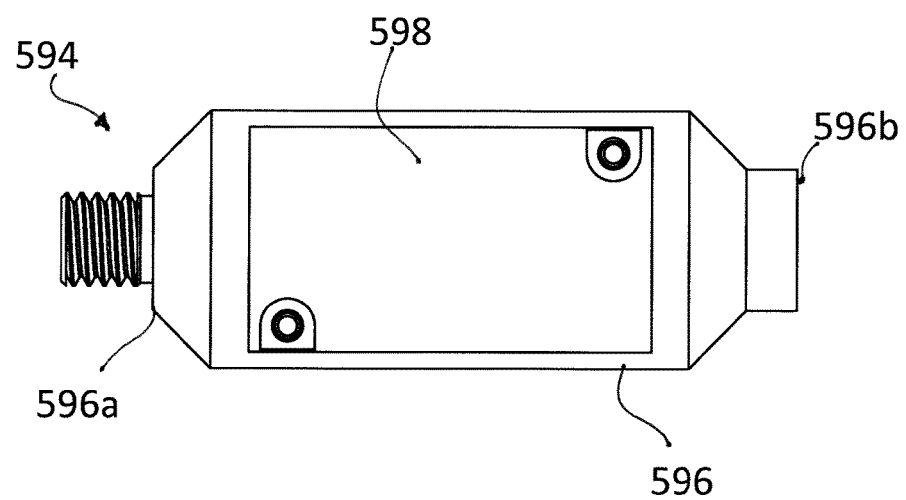
FIG. 33 is a plan view of a vocal training attachment member for use with the vocal training device of FIG. 30.
Figure 34:
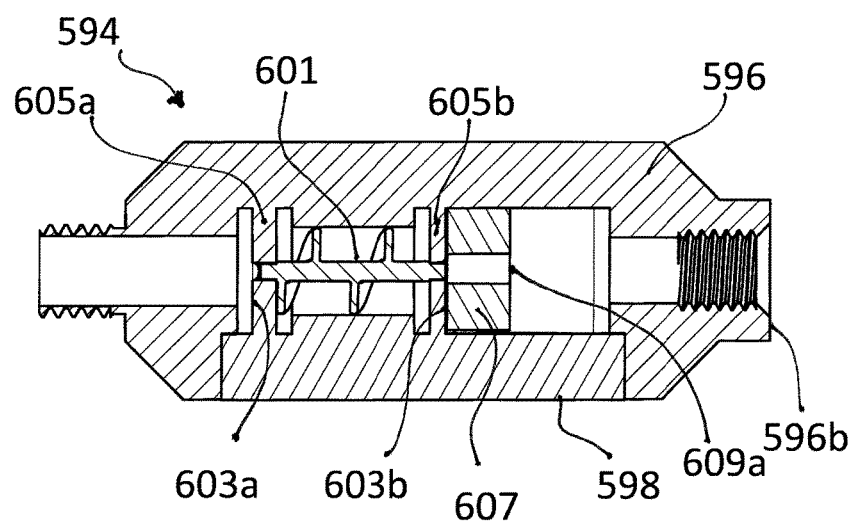
FIG. 34 is a section view of the vocal training attachment member of FIG. 33.
Figure 35:
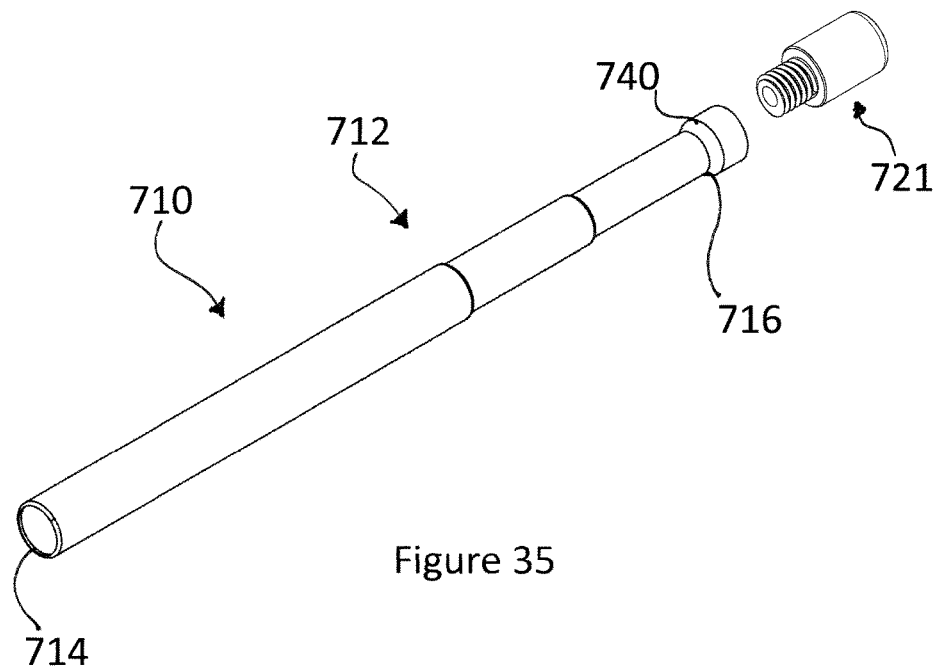
FIG. 35 is a partially exploded isometric view of a vocal training device according to a seventh embodiment of the present invention.
Figure 36:
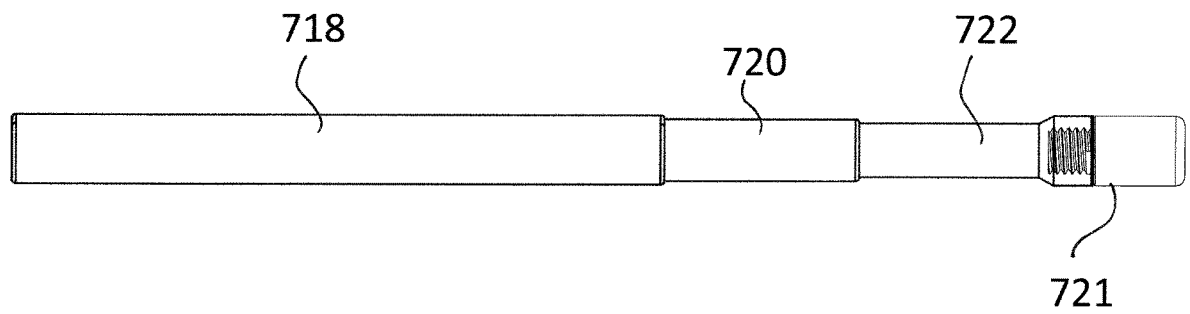
FIG. 36 is a plan view of the vocal training device of FIG. 35.
Figure 37:
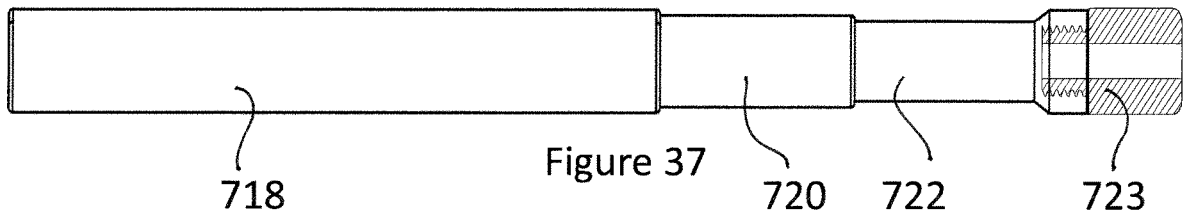
FIG. 37 is a section view of the vocal training device of FIG. 35.
Figure 38:
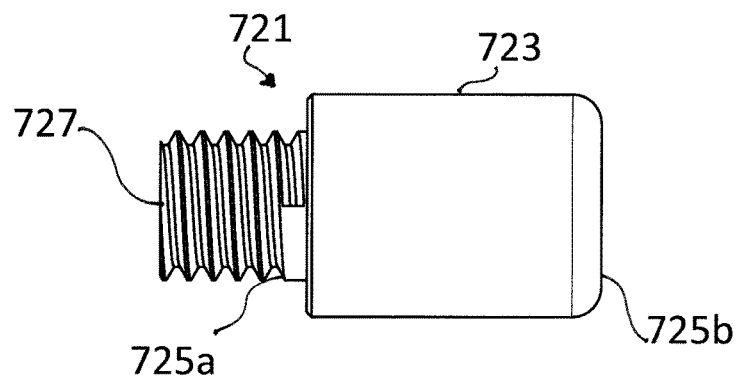
FIG. 38 is a plan view of a vocal training attachment member for use with the vocal training device of FIG. 35.
Figure 39:
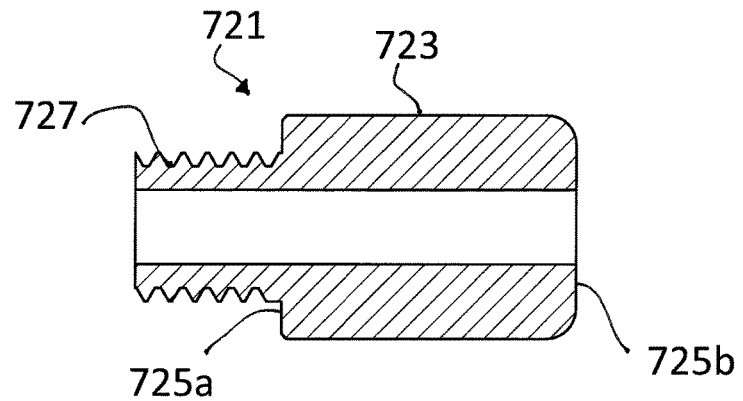
FIG. 39 is a section view of the vocal training attachment member of FIG. 38.
Figure 40:
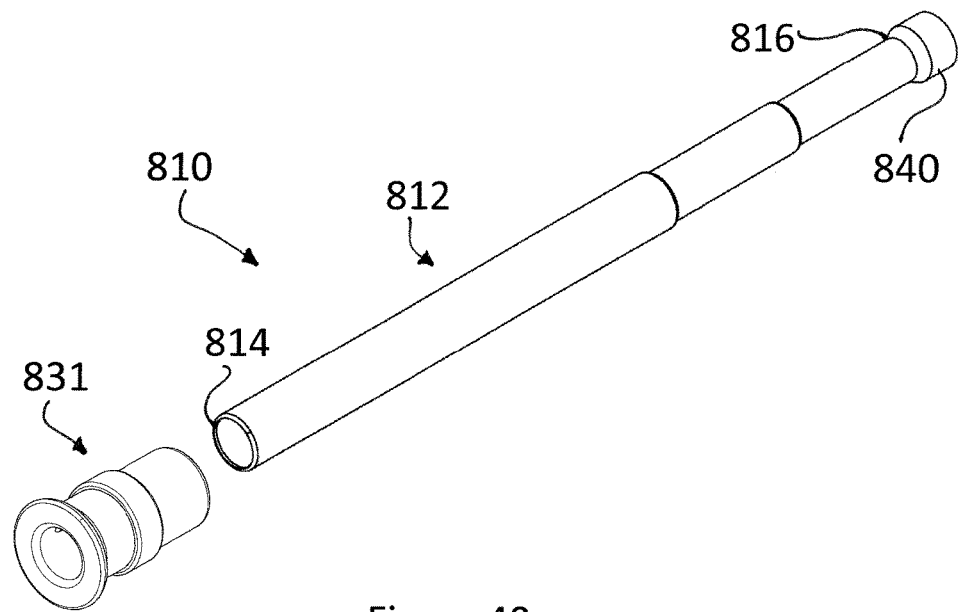
FIG. 40 is a partially exploded isometric view of a vocal training device according to an eighth embodiment of the present invention.
Figure 41:
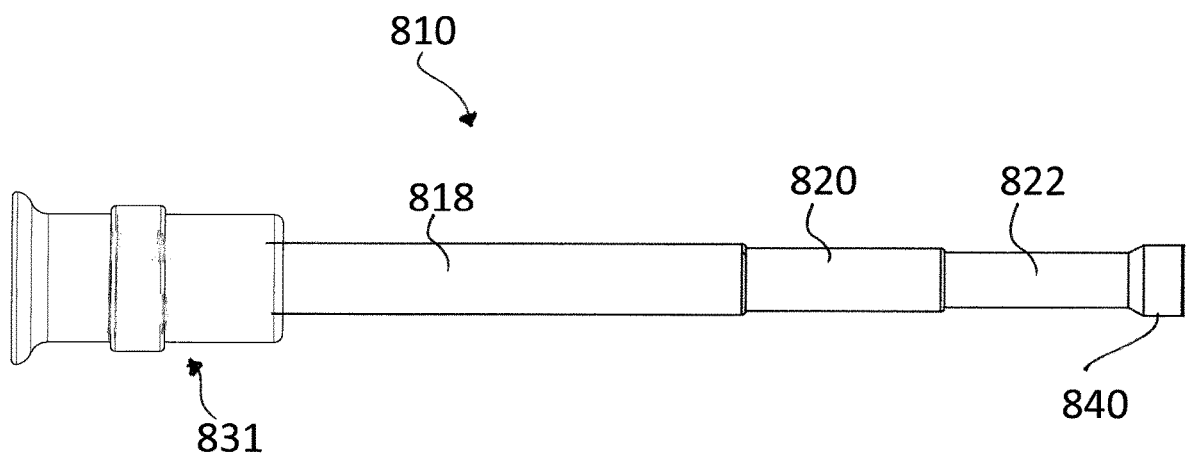
FIG. 41 is a plan view of the vocal training device of FIG. 40.
Figure 42:
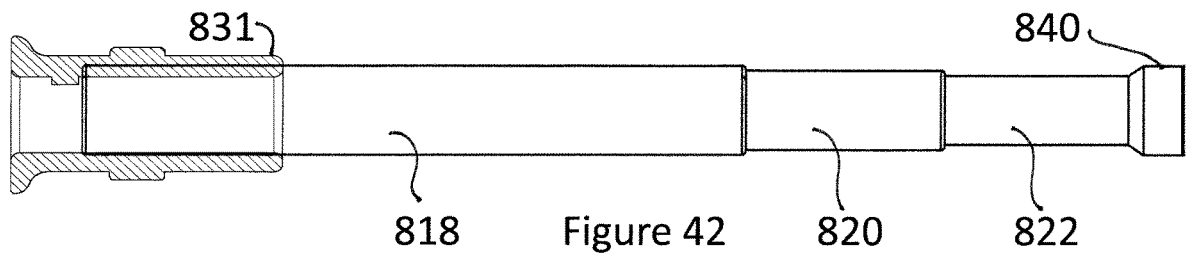
FIG. 42 is a section view of the vocal training device of FIG. 40.
Figure 43:
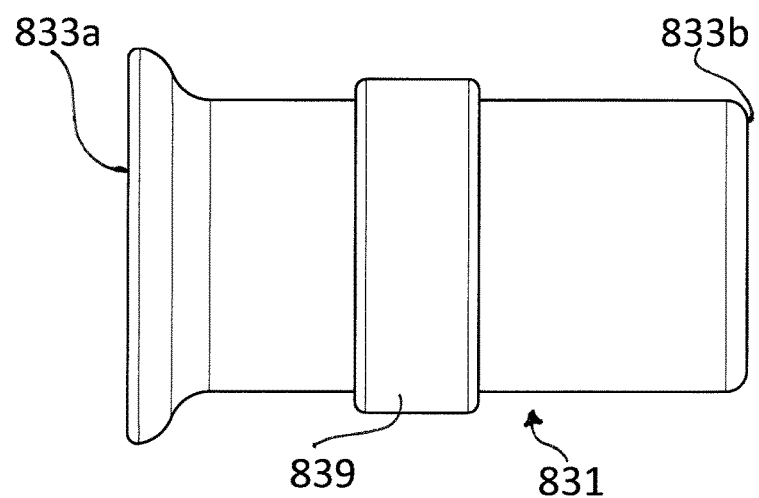
FIG. 43 is a plan view of a vocal training attachment member for use with the vocal training device of FIG. 40.
Figure 44:
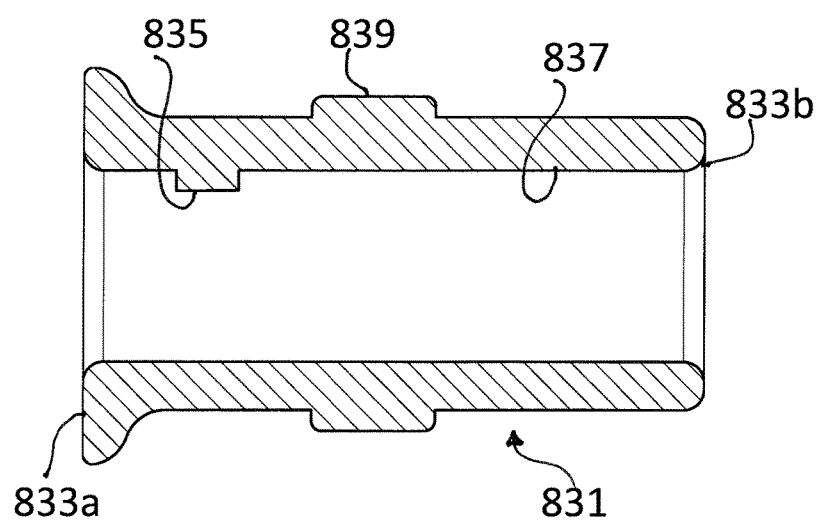
FIG. 44 is a section view of the vocal training attachment member of FIG. 43.

With particular reference to FIGS. 17, 18 and 19, the vocal training attachment member 242 has a generally cylindrical hollow body 258 having a first end 260 and a second end 262. Each of the first end 260 and the second end 262 of the generally cylindrical body 258 is open. The generally cylindrical hollow body 258 has an outer frame 264 on which a fan 266 is mounted.

The vocal training attachment member 242 of the third embodiment of the invention is a breath visualisation attachment to assist a user with vocal training exercises as will be described below.

The vocal training device 210 is manufactured and assembled as follows.

Each of the first tube member 218, the second tube member 220, the third tube member 222, the first telescopic connector 236, the second telescopic connector 238, the connector 240 and the vocal training attachment member 242 is manufactured from a suitable reusable material, for example a metal such as stainless steel.

In some examples of the invention, the stainless steel may be an austenitic grade stainless steel, such as stainless steel 304, for example food grade stainless steel.

The first telescopic connector 236 is installed within the hollow interior of the first tube member 218. A first 'O' ring is placed at either end of the first telescopic connector 236. Similarly, the second telescopic connector 238 is installed within the hollow interior of the second tube member 220. A second 'O' ring is placed at either end of the second telescopic connector 238.

The first end 228 of the second tube member 220 is positioned within the second end 226 of the first tube member 218 such that the outer wall of the second tube member 220 engages an 'O' ring of the first telescopic connector 236. The second tube member 220 can thus be slidably moved within the hollow interior of the first tube member 218.

The first end 232 of the third tube member 222 is positioned within the second end 230 of the second tube member 220 such that the third tube member 222 engages an 'O' ring of the second telescopic connector 238. The third tube member 222 can thus be slidably moved within the hollow interior the second tube member 220.

The vocal training device 210 can, therefore, be moved between a compact configuration (in which the third tube member 222 is positioned fully within the second tube member 220 and the second tube member 220 is positioned fully within the first tube member 218) and an extended configuration (in which the second tube member 220 extends from the second end 226 of the first tube member 218 and the third tube member 222 extends from the second end 230 of the second tube member 220).

It will be understood that, in the compact configuration, the second end 226 of the first tube member 218, the second end 230 of the second tube member 220 and the second end 234 of the third tube member 222 are co-located with the second end 216 of the generally cylindrical hollow body 212.

In the extended configuration, only the second end 234 of the third tube member 222 is co-located with the second end 216 of the generally cylindrical hollow body 212.

In a configuration that is intermediate the compact configuration and the extended configuration, the 'intermediate configuration', the second end 230 of the second tube member 220 and the second end 234 of the third tube member 222 are co-located with the second end 216 of the generally cylindrical hollow body 212.

The generally cylindrical hollow body 212 can thus have three different lengths, according to the positions of the telescopic first, second and third tube members 218, 220, 222.

The first end 246 of the connector 240 is positioned within the second end 234 of the third tube member 222 such that the intermediate portion 254 of the connector 240 abuts the second end 234 of the third tube member 222. The connector 240 is held in place within the third tube member 222 by any suitable fastening means, for example a push-fit fastening or a screw thread fastening.

The vocal training attachment member 242 is then fastened to the connector 240 by inserting the first end 260 of the vocal training attachment member 242 within the second flared portion 252 of the connector 240. The vocal training attachment member 242 is held in place within the second portion 252 of the connector 240 by any suitable fastening means, for example a push-fit fastening or a screw thread fastening.

Since each of the first tube member 218, the second tube member 220, the third tube member 222, the connector 240 and the vocal training attachment member 242 are open at each end, the vocal training device 210 is a hollow tube or cylinder or pipe and thus air (or any other fluid or flowable, low viscosity, substance) can be drawn from the second end 262 of the vocal training attachment member 242 to the first end 224 of the first tube member 218 (which is co-located with the first end 214 of the generally cylindrical hollow body 212 of the vocal training device 210). Similarly, air (or any other fluid or flowable, low viscosity, substance) can be drawn from the first end 224 of the first tube member 218 to the second end 262 of the vocal training attachment member 242. In other words, the vocal training device 210 is a straw-like device.

The 'O' rings ensure that the joints between the first, second and third tube members 218, 220, 222 are sealed to prevent the escape of air, water or other fluid from the joints.

Use of the vocal training device 210 for vocal training exercises will now be described.

As described in relation to the first embodiment, the telescopic arrangement of the first, second and third tube members 218, 220, 222 allows the resistance of the vocal training device 210 to be easily adjusted according to a user's requirements. The longer the length of the device 210, the greater the resistance it will have. In contrast, the shorter the length of the device 210, the less resistance it will have.

Therefore, to increase the resistance, a user can place the vocal training device 210 in its extended configuration (in which the second tube member 220 extends fully from the second end 226 of the first tube member 218 and the third tube member 222 extends fully from the second end 230 of the second tube member 220).

In order to reduce the resistance, a user can place the vocal training device 210 in its compact configuration (in which the third tube member 222 is positioned fully within the second tube member 220 and the second tube member 220 is positioned fully within the first tube member 218).

The resistance achieved can clearly be optimised according to a user's requirements by varying the position of the second tube member 220 relative to the first tube member 218 and/or by varying the position of the third tube member 222 relative to the second tube member 220. In one exemplary arrangement, the 'intermediate configuration', the third tube member 222 may be fully contracted within the second tube member 220 and the second tube member 220 may be fully extended relative to the first tube member 218.

The fan 266 advantageously provides a biofeedback mechanism. With the fan 266 mounted on the frame 264 on the exterior surface of the breath visualisation attachment 242, a user is able to visualise their airflow in real time, which is not generally possible without the need for either specialised scientific equipment, or by placing a device in water and monitoring the bubbles produced during use of the device. This biofeedback is an essential part of understanding and controlling airflow, which is vital for singing correctly. It allows the user to very accurately see and respond to something previously 'invisible'. The breath visualisation attachment provides a very compact, portable solution.

If desired, the fan 266 can also be used with water in order to generate resistance. This is because a user will need to displace the water and rotate the fan whilst breathing out, which is more difficult to do as compared to either displacing the water or rotating the fan.

The vocal training device 210 is thus advantageous as it is versatile, yet less complex than other variable resistance SOVT training devices.

A fourth embodiment of the present invention will now be described with reference to FIGS. 20 to 24.

The vocal training device 310 of the fourth embodiment has a generally cylindrical hollow body 312. The generally cylindrical hollow body 312 comprises a first end 314 and a second end 316. Each of the first end 314 and the second end 316 are open. The generally cylindrical body 312 and the connector 340 are like the connector 40 of the first embodiment and so will not be described further.

The vocal training attachment member is a variable aperture reducing attachment member 372 having a generally cylindrical hollow body 384 open at a first, connecting end 382a and closed at a second end 382b. The first connecting end 382a carries a threaded portion for connection to a complementary threaded portion on the connector 340. The generally cylindrical hollow body 384 is formed with two rows of openings 374 each opening being of different diameter. Openings 374a, 374b, 374c are included in a first row of different diameters. An outer sleeve 376 formed with slot 378 is fitted over the body 384. The outer sleeve 376 is rotatable around the body 384 to expose a single opening 374a which acts as the aperture for air flowing out of the device 310 in use. Rotation of the outer sleeve 376 around the body 384 brings the slot 378 into alignment with a different sized opening, 374b or 374c, depending on the degree of rotation. Openings 374e, 375g in the second row are offset with respect to the first row openings so that only one opening at a time is exposed through the slot 378. Each opening 374 is associated with a marker 380 visible through the slot 378 when in alignment to show a user which aperture setting is currently selected.

As described with reference to earlier embodiments which have common components, the telescopic arrangement of the first, second and third tube members 318, 320, 322 allows the resistance of the vocal training device 310 to be adjusted according to a user's requirements. In relation to the illustrated fourth embodiment, a user can further adjust, or "fine tune", the resistance by rotating the outer sleeve 376 to align the slot 378 with different openings. Once a user has arrived at an optimum setting for their requirements, they can note which opening has been selected by referring to the marker 380 adjacent the opening.

The vocal training device 310 is thus advantageous, offering a range of fixed openings which a user can return to according to their preference.

A fifth embodiment of the present invention will now be described with reference to FIGS. 25 to 29.

The vocal training device 410 of the fifth embodiment has a generally cylindrical hollow body 412. The generally cylindrical hollow body 412 comprises a first end 414 and a second end 416. Each of the first end 414 and the second end 416 are open. The generally cylindrical body 412 and the connector 440 are like the connector 40 of the first embodiment and so will not be described further.

As also described with reference to earlier embodiments which have common components, the telescopic arrangement of the first, second and third tube members 418, 420, 422 allows the resistance of the vocal training device 410 to be adjusted according to a user's requirements. In relation to this fifth embodiment, the vocal training attachment member is a WRVT training adapter 486 for enabling the device 410 to be used with water.

The WRVT training adapter 486 is curved tubular extension member having a threaded portion at its distal end 488a for connection to a complementary threaded portion on the connector 440. A first extension portion 490a of the adapter 486 adjacent the threaded portion aligns with the longitudinal axis of the generally cylindrical hollow body 412 when fitted. Adjoining the first, straight extension portion 490a is a curved portion 492, which in turn adjoins with a second, straight extension portion 490b terminating in proximal end 488b. The second extension portion 490b is used as a mouthpiece allowing the hollow cylindrical body 412 to be in a substantially vertical orientation when a user adopts a normal, upright posture. In use, the first end 414 of the body 412 can be submersed in water in the same vertical orientation to enable the user to train under variable resistance conditions through generation of bubbles.

A sixth embodiment of the invention will now be described with reference to FIGS. 30 to 34.

The vocal training device 510 of the sixth embodiment has a generally cylindrical hollow body 512. The generally cylindrical hollow body 512 comprises a first end 514 and a second end 516. Each of the first end 514 and the second end 516 are open. The generally cylindrical body 512 and the connector 540 are like the connector 40 of the first embodiment and so will not be described further.

As also described with reference to earlier embodiments which have common components, the telescopic arrangement of the first, second and third tube members 518, 520, 522 allows the resistance of the vocal training device 510 to be adjusted according to a user's requirements. In relation to this sixth embodiment, the vocal training attachment member is an oscillating resistance generator 594 for enabling a user to mimic WRVT exercises without the need for water.

The oscillating resistance generator 594 has a generally cylindrical hollow housing 596 with a lid 598 for access to the interior of the housing. The housing 596 has a first end 596a adjacent a threaded portion for connection to connector 540 and a second end 596b which has an internal thread for connecting to other vocal training attachment members.

The housing 596 accommodates an air flow moderator that takes the form of a rotatable spiral fan element 601 which is held in position by lugs 603a, 603b on the interior wall of the lid 598 and opposing lugs 605a, 605b on the interior wall of the housing 596, and a fixed aperture plate 607 provided with two apertures 609a, 609b (not visible) of differing diameters through which air is alternately directed in use by the rotating spiral fan element 601. The aperture plate 607 may be substituted with a different aperture plate having differently sized apertures according to the individual preference of the user.

The spiral fan element 601 is freely rotatable under the air flow generated by the user and the user experiences an oscillating resistance as the air is directed towards each of the apertures 609a, 609b alternately as the fan element rotates. The user is therefore able to have a similar vocal training experience to that encountered through use of water, but the device 510 can be used anywhere without the need for water.

A seventh embodiment of the invention will now be described with reference to FIGS. 35 to 39.

The vocal training device 710 of the seventh embodiment has a generally cylindrical hollow body 712. The generally cylindrical hollow body 712 comprises a first end 714 and a second end 716. Each of the first end 714 and the second end 716 are open. The generally cylindrical body 712 and the connector 740 are like the connector 40 of the first embodiment and so will not be described further.

As also described with reference to earlier embodiments which have common components, the telescopic arrangement of the first, second and third tube members 718, 720, 722 allows the resistance of the vocal training device 710 to be adjusted according to a user's requirements. In relation to this seventh embodiment, the device 710 includes a mouth piece 721 in the form of a hollow cylindrical attachment 723 which is removably connectable to the connector 740 at its distal end 725a by a threaded portion 727.

The internal diameter of the hollow cylindrical attachment 723 is uniform between the distal end 725a and proximal end 725b. The mouth piece 721 has a greater external diameter compared to the second end 716 of the generally hollow cylindrical body 712 to provide a more comfortable interface for the user. Alternative mouth pieces may be made available, with the dimensions of the mouth piece 721 varied to suit an individual user's preference, both in relation to the internal diameter and external diameter.

An eighth embodiment of the invention will now be described with reference to FIGS. 40 to 44.

The vocal training device 810 of the eighth embodiment has a generally cylindrical hollow body 812. The generally cylindrical hollow body 812 comprises a first end 814 and a second end 816. Each of the first end 814 and the second end 816 are open. The generally cylindrical body 812 and the connector 840 are like the connector 40 of the first embodiment and so will not be described further.

As also described with reference to earlier embodiments which have common components, the telescopic arrangement of the first, second and third tube members 818, 820, 822 allows the resistance of the vocal training device 810 to be adjusted according to a user's requirements. In relation to this eighth embodiment, the device 810 includes a mouth piece adapter 831 which is adapted to provide an interference fit with the first end 814 of the hollow cylindrical body 812, and with an end of another vocal training device having a hollow tubular portion which has a wider internal diameter. The other vocal training device could be a voice mask, for example.

The distal end 833b of the mouth piece adapter 831 fits over the first end 814 of the hollow cylindrical body 812. An abutment in the form of protrusion 835 is formed on the internal wall 837 of the adapter to prevent the first end 814 of the hollow cylindrical body from exiting the adapter at its proximal end 833a. At this position, the mouth piece adapter is securely retained on the first end 814.

The proximal end 833a of the mouth piece adapter is outwardly flared for the comfort of the user.

A collar 839 is fitted around the mid-portion of the mouth piece adapter 831. The collar 839 serves as an abutment against which an end of a hollow tubular portion of an alternative vocal training device of wider internal diameter rests when the adapter 831 is fitted thereto. In this latter use, the distal end 833b is inserted into the (wider) hollow tubular portion. The mouth piece adapter 831 can therefore be used with different types and/or different diameter vocal training devices.

The vocal training attachment members 42, 142, 242, 372, 486, 594, mouth piece 721 and mouth piece adapter 831 as illustrated herein across FIGS. 1 to 44 can also be used independently of the generally cylindrical hollow bodies of the vocal training devices shown in the accompanying drawings, and instead can be attached to other vocal training devices. While the vocal training attachment members and mouth piece are shown with threaded connecting portions, these connecting portions may be replaced with alternative connecting portions, for example, for connecting to other devices by means of an interference or resistance fit. Such alternative connecting arrangements are within the knowledge of the skilled person.

Figure 45:
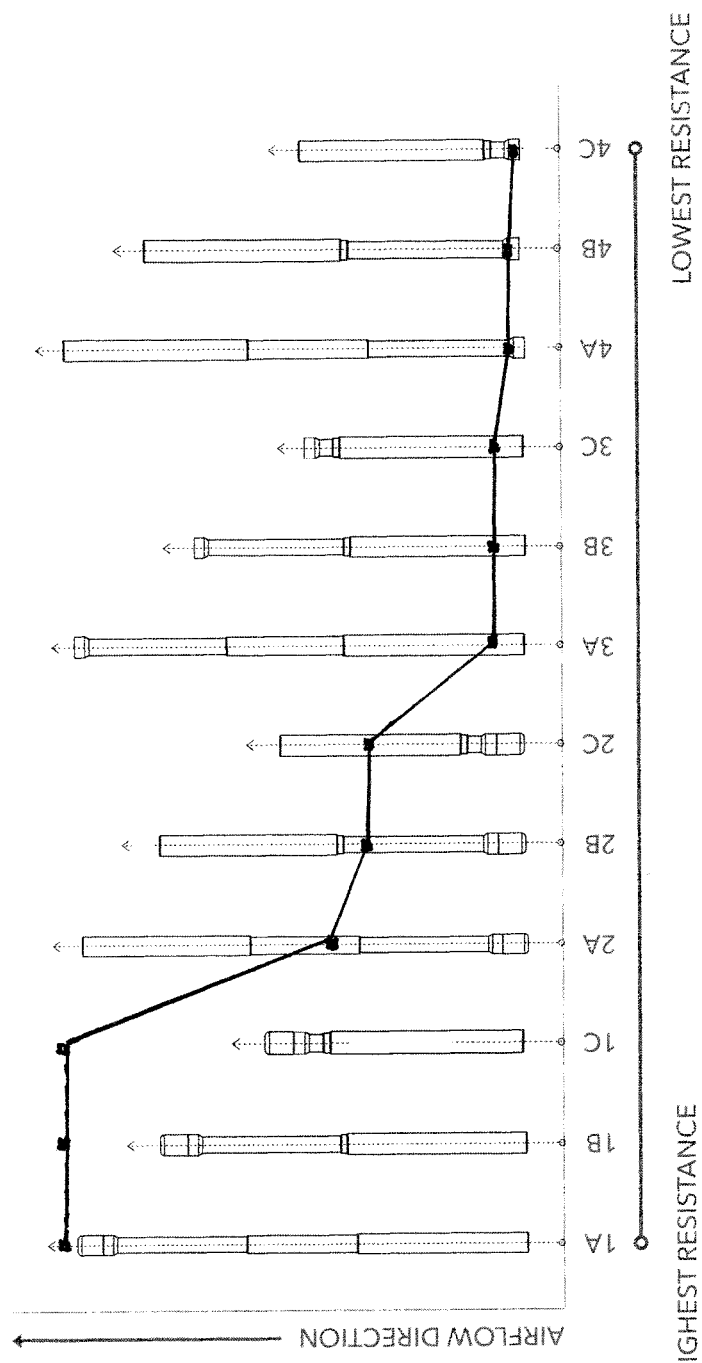
FIG. 45 is a schematic representation showing how resistance is affected by direction of airflow and length using a device according to an embodiment of the invention.

Referring to FIG. 45, there is shown twelve different resistance settings that are achievable simply by adjusting the orientation (air flow direction) and extension of the first, second and third tube members of the vocal training device of FIG. 1 and including or omitting the vocal attachment member 42. Variations fall within the scope of the invention.

In the embodiments described, the generally cylindrical hollow bodies 12, 112, 212, etc. of the vocal training devices 10, 110, 210, etc. each include three tube members. It will be understood that in alternative embodiments of the invention, any number of telescopic tube members may be provided. In some embodiments of the invention, two telescopic tube members may be provided. In other embodiments of the invention, more than three telescopic tube members may be provided.

The invention claimed is:

1. A vocal training device comprising:
   a telescopic cylindrical hollow body having:
      a first open end;
      a second open end;
      a first tube member having the first open end; and,
      a second tube member having the second open end;
   wherein the second tube member is configured to be telescopically inserted into the first tube member, such that a length of the telescopic cylindrical hollow body of the vocal training device is adjustable; and,
   wherein the vocal training device further comprises:
      a connector having a portion that is configured for removable connection to the second open end of the telescopic cylindrical hollow body of the vocal training device and
      a vocal training attachment member that is configured for removable connection to the connector.

2. The vocal training device according claim 1, wherein the vocal training attachment member is an aperture reducing attachment.

3. The vocal training device according to claim 2, wherein the aperture reducing attachment is a variable aperture reducing attachment.

4. The vocal training device according to claim 3, wherein the variable aperture reducing attachment includes an attachment member provided with a plurality of openings having a range of different diameters.

5. The vocal training device according to claim 4, wherein the variable aperture reducing attachment includes an outer sleeve having a slot.

6. The vocal training device according to claim 5, wherein the outer sleeve is configured to be rotatable relative to the variable aperture attachment such that as the sleeve is rotated the slot aligns with different openings of the plurality of openings.

7. The vocal training device according to claim 3, wherein the variable aperture reducing attachment includes a slot.

8. The vocal training device according to claim 7, wherein the slot is triangular.

9. The vocal training device according to claim 3, wherein the variable aperture reducing attachment includes an outer sleeve having a rectangular opening.

10. The vocal training device according to claim 9, wherein the outer sleeve is configured to be rotatable relative to the variable aperture reducing attachment such that the position of the rectangular opening relative to the slot is capable of being varied.

11. The vocal training device according to claim 1, wherein the telescopic cylindrical hollow body has a first internal diameter at the first open end and a second internal diameter at the second open end, wherein the second internal diameter is less than the first internal diameter.

12. The vocal training device according to claim 11, wherein the connector has a third internal diameter, wherein the third diameter is greater than the second diameter.

13. The vocal training device according to claim 1, the vocal training device further comprising:
a third tube member;
wherein the third tube member is configured to be telescopically inserted into the second tube member, such that the length of the telescopic cylindrical hollow body of the vocal training device is adjustable.

14. The vocal training device according to claim 1, wherein the portion of the connector that is configured for removable connection to the second open end of the telescopic cylindrical hollow body is a first portion, and the connector also has a second portion that is flared such that an outer diameter of the second portion is greater than an outer diameter of the first portion.

15. The vocal training device according to claim 1, wherein the vocal training attachment member is a breath visualisation attachment.

16. The vocal training device according to claim 1, wherein the vocal training attachment member is a water resistance voice therapy (WRVT) training adapter.

17. The vocal training device according to claim 1, wherein the vocal training attachment member is an oscillating resistance generator.

18. The vocal training device according to claim 1, further comprising a mouth piece configured for removable connection to an open end of the telescopic cylindrical hollow body or to the connector of the vocal training device.

19. A vocal training system comprising:
a mouth piece; and
a vocal training device comprising:
  a telescopic cylindrical hollow body having:
  a first open end;
  a second open end;
  a first tube member having the first open end; and,
  a second tube member having the second open end;
  wherein the second tube member is configured to be telescopically inserted into the first tube member, such that a length of the telescopic cylindrical hollow body of the vocal training device is adjustable; and,
wherein the vocal training device further comprises:
  a connector having a portion that is configured for removable connection to the second open end of the telescopic cylindrical hollow body of the vocal training device and
  a vocal training attachment member that is configured for removable connection to the connector,
  wherein the vocal training attachment member comprises one or more vocal training attachment members selected from a group consisting of: an aperture reducing attachment, a variable aperture reducing attachment, a breath visualisation attachment, a water resistance voice therapy training adapter, and an oscillating resistance generator.

* * * * *